(12) United States Patent
Kennedy et al.

(10) Patent No.: US 10,385,212 B2
(45) Date of Patent: Aug. 20, 2019

(54) SILICONE EMULSIONS

(71) Applicant: Dow Corning Corporation, Midland, MI (US)

(72) Inventors: Robert D. Kennedy, Midland, MI (US); Bertrand Louis Julien Lenoble, Silly (BE); Donald Taylor Liles, Midland, MI (US); Yihan Liu, Midland, MI (US); Elodie Raynaud, Epinois (BE)

(73) Assignee: Dow Silicones Corporation, Midland, MI (US)

( * ) Notice: Subject to any disclaimer, the term of this patent is extended or adjusted under 35 U.S.C. 154(b) by 173 days.

(21) Appl. No.: 15/327,274

(22) PCT Filed: Jul. 22, 2015

(86) PCT No.: PCT/US2015/041443
§ 371 (c)(1),
(2) Date: Jan. 18, 2017

(87) PCT Pub. No.: WO2016/014609
PCT Pub. Date: Jan. 28, 2016

(65) Prior Publication Data
US 2017/0204266 A1 Jul. 20, 2017

Related U.S. Application Data

(60) Provisional application No. 62/027,959, filed on Jul. 23, 2014.

(51) Int. Cl.
| | |
|---|---|
| *C08L 83/12* | (2006.01) |
| *C08L 71/02* | (2006.01) |
| *C08J 3/03* | (2006.01) |
| *C08L 83/04* | (2006.01) |
| *C08J 3/05* | (2006.01) |
| *C09D 175/00* | (2006.01) |
| *A61Q 19/00* | (2006.01) |
| *A61K 8/891* | (2006.01) |
| *A61K 8/894* | (2006.01) |
| *A61K 8/06* | (2006.01) |
| *C09D 175/04* | (2006.01) |
| *C08G 65/08* | (2006.01) |
| *C08G 65/336* | (2006.01) |
| *C08G 77/46* | (2006.01) |
| *C08G 77/16* | (2006.01) |

(52) U.S. Cl.
CPC ............ *C08L 83/12* (2013.01); *A61K 8/06* (2013.01); *A61K 8/891* (2013.01); *A61K 8/894* (2013.01); *A61Q 19/00* (2013.01); *C08G 65/08* (2013.01); *C08G 65/336* (2013.01); *C08G 77/46* (2013.01); *C08J 3/03* (2013.01); *C08J 3/05* (2013.01); *C08L 71/02* (2013.01); *C08L 83/04* (2013.01); *C09D 175/00* (2013.01); *C09D 175/04* (2013.01); *A61K 2800/10* (2013.01); *C08G 77/16* (2013.01); *C08J 2383/04* (2013.01); *C08J 2483/06* (2013.01); *C08J 2483/12* (2013.01); *C08L 2201/52* (2013.01); *C08L 2205/025* (2013.01)

(58) Field of Classification Search
CPC combination set(s) only.
See application file for complete search history.

(56) References Cited

U.S. PATENT DOCUMENTS

| | | | |
|---|---|---|---|
| 2,823,218 A | 2/1958 | Speier | |
| 2,857,356 A | 10/1958 | Goodwin, Jr. | |
| 3,159,601 A | 12/1964 | Ashby | |
| 3,220,972 A | 11/1965 | Lamoreaux | |
| 3,296,291 A | 1/1967 | Chalk et al. | |
| 3,419,593 A | 12/1968 | Willing | |
| 3,516,946 A | 6/1970 | Modic | |
| 3,715,334 A | 2/1973 | Karstedt | |
| 3,814,730 A | 6/1974 | Karstedt | |
| 3,923,705 A | 12/1975 | Smith | |
| 3,989,668 A | 11/1976 | Lee et al. | |
| 4,584,337 A * | 4/1986 | Lee | C08F 290/068 524/457 |
| 4,584,355 A | 4/1986 | Blizzard et al. | |
| 4,585,836 A | 4/1986 | Homan et al. | |
| 4,591,622 A | 5/1986 | Blizzard et al. | |
| 4,597,894 A * | 7/1986 | Abe | B01D 19/0409 106/287.16 |
| 4,784,879 A | 11/1988 | Lee et al. | |
| 4,871,529 A * | 10/1989 | Sramek | A61K 8/046 424/47 |
| 5,015,469 A * | 5/1991 | Yoneyama | A61K 8/06 424/59 |
| 5,035,832 A | 7/1991 | Takamura et al. | |
| 5,036,117 A | 7/1991 | Chung et al. | |
| 5,175,325 A | 12/1992 | Brown et al. | |
| 5,192,336 A | 3/1993 | Grewal | |
| 5,726,256 A | 3/1998 | Benson et al. | |
| 5,776,614 A | 7/1998 | Cifuentes et al. | |
| 5,861,472 A | 1/1999 | Cifuentes et al. | |
| 5,869,556 A | 2/1999 | Cifuentes et al. | |

(Continued)

FOREIGN PATENT DOCUMENTS

| | | |
|---|---|---|
| CN | 103025834 A | 4/2013 |
| CN | 103182271 A | 7/2013 |

(Continued)

OTHER PUBLICATIONS

Machine translation of JP 09-296045 A, retrieved Aug. 2018 (Year: 2018).*

(Continued)

*Primary Examiner* — Nicole M. Buie-Hatcher
(74) *Attorney, Agent, or Firm* — Warner Norcross & Judd LLP

(57) ABSTRACT

The present invention provides water dilutable silicone emulsions comprising a silicone and a silicone polyether; a coating composition comprising the emulsions; a process of making the emulsions; and uses of the emulsions.

22 Claims, No Drawings

(56) References Cited

U.S. PATENT DOCUMENTS

| | | | |
|---|---|---|---|
| 5,955,003 A * | 9/1999 | Terren | A61K 8/06 424/401 |
| 6,210,690 B1 * | 4/2001 | Nabeshima | A61K 8/06 424/401 |
| 6,337,086 B1 | 1/2002 | Kanios et al. | |
| 6,372,830 B1 * | 4/2002 | Sato | A61K 8/06 424/401 |
| 7,019,069 B2 * | 3/2006 | Kobayashi | C09D 183/04 524/266 |
| 7,186,406 B2 * | 3/2007 | Decoster | A61K 8/8158 424/70.12 |
| 7,887,834 B2 | 2/2011 | Lin et al. | |
| 2006/0135626 A1 | 6/2006 | Shim et al. | |
| 2007/0219318 A1 | 9/2007 | Lin et al. | |
| 2008/0194705 A1 | 8/2008 | Ahmad et al. | |
| 2013/0122204 A1 | 5/2013 | Evans et al. | |

FOREIGN PATENT DOCUMENTS

| | | | |
|---|---|---|---|
| EP | 0347895 A2 | 12/1989 | |
| EP | 0902044 A2 | 3/1999 | |
| JP | 09296045 A * | 11/1997 | |
| JP | 2000219608 A * | 8/2000 | |
| WO | WO-9922699 A1 * | 5/1999 | ............. A61K 8/068 |
| WO | WO2005103117 A1 | 11/2005 | |
| WO | WO2007145996 A2 | 12/2007 | |
| WO | WO2008144084 A2 | 11/2008 | |
| WO | WO2010075244 A1 | 7/2010 | |
| WO | WO-2013092382 A1 * | 6/2013 | ............... A61Q 5/00 |
| WO | WO2014058887 A1 | 4/2014 | |

OTHER PUBLICATIONS

Machine translation of JP 2000-219608 A, retrieved Aug. 2018 (Year: 2018).*

English language abstract and machine translation for CN103182271(A) extracted from http://worldwide.espacenet.com database on Jun. 7, 2018, 11 pages.

PCT/US2015/041443 International Search Report dated Oct. 16, 2015, 6 pages.

* cited by examiner

SILICONE EMULSIONS

CROSS-REFERENCE TO RELATED APPLICATIONS

This application is the National Stage of International Application No. PCT/US2015/041443 filed on 22 Jul. 2015, which claims priority to and all advantages of U.S. Provisional Application No. 62/027,959 filed on 23 Jul. 2014, the contents of which are hereby incorporated by reference.

FIELD OF THE INVENTION

The present invention is in the field of silicone emulsions having a high viscosity silicone and a silicone polyether. The emulsions of the present invention can be used in the field of coatings and in personal care applications.

BACKGROUND OF THE INVENTION

Preparation of aqueous mechanical emulsions of high molecular weight silicones is difficult due to the high viscosity of the silicone material. The emulsions are typically prepared using specialized surfactants or with the need to dilute the high viscosity silicone in a solvent which may be undesirable, such as volatile organic compounds, aromatic solvent or other environmentally unfriendly substances. High molecular weight silicones can also be emulsified using specialized equipment such as twin screw extruders. However, the costs for such equipment are relatively high, both from a capital and an operational standpoint.

Thus, there exists a need to identify materials and processes to prepare emulsions of high molecular weight silicones that do not require specialized surfactants or undesirable solvents, nor require expensive emulsification equipment.

SUMMARY OF THE INVENTION

The present invention provides water dilutable silicone emulsions comprising:
A) 10 to 95 weight percent of a silicone having a viscosity of at least 1,000,000 cP at 25° C.;
B) 0.1 to 30 weight percent of a silicone polyether;
C) optionally sufficient amount of water to sum all ingredients of the emulsions to 100 weight percent;
D) optionally a co-surfactant; and
E) optionally a co-solvent.

The water C) may be from 0 to 90 weight percent; the co-surfactant D) may be from 0 to 30 weight percent; and the co-solvent E) may be from 0 to 30 weight percent. In one embodiment the co-solvent is a non-aqueous polar co-solvent.

The present invention also provides water dilutable silicone emulsions comprising:
A) 10 to 95 weight percent of a silicone;
B) 0.1 to 30 weight percent of a silicone polyether obtainable by reacting
  i) SiH functional polyorganosiloxane,
  ii) monoalkenyl functional polyoxyalkylene,
  iii) dialkenyl functional polyorganosiloxane,
  wherein the molar ratio of SiH to alkenyl in (ii) is from 1:0.5 to 1:1.5 and the molar ratio of SiH to alkenyl in (iii) is from 1:0.01 to 1:0.5 with the proviso that the total alkenyl:SiH is from 1.5:1 to 1:1;
C) optionally sufficient amount of water to sum all ingredients of the emulsions to 100 weight percent;
D) optionally a co-surfactant; and
E) optionally a co-solvent.

The dialkenyl functional polyorganosiloxane may be an optional component. The ratio of the co-surfactant D) to the silicone polyether B) is no greater than 5. The ratio of the co-solvent E) to the silicone polyether B) is no greater than 5. In one embodiment the co-solvent is a non-aqueous polar co-solvent.

The present invention also provides coating compositions comprising the silicone emulsions and processes for making the silicone emulsions.

DETAILED DESCRIPTION OF THE INVENTION

As used herein, "weight percent" refers to the weight of an ingredient relative to the total weight of the silicone emulsion, unless indicated otherwise.

The term "comprising" is used herein in its broadest sense to mean and to encompass the notions of "include" and "consist of."

The use of "for example" or "such as" to list illustrative examples does not limit to only the listed examples. Thus, "for example" or "such as" means "for example, but not limited to" or "such as, but not limited to" and encompasses other similar or equivalent examples.

The term "substituted" as used in relation to another group, for example, an alkyl group, means, unless indicated otherwise, one or more hydrogen atoms in the alkyl group has been replaced with another substituent. Examples of such substituents include, an alkyl group having 1 to 6 carbon atoms, halogen atoms such as chlorine, fluorine, bromine, and iodine; halogen atom containing groups such as chloromethyl, perfluorobutyl, trifluoroethyl, and non-afluorohexyl; oxygen atoms; oxygen atom containing groups such as (meth)acrylic and carboxyl; nitrogen atoms; nitrogen atom containing groups such as amines, amino-functional groups, amido-functional groups, and cyano-functional groups; sulphur atoms; and sulphur atom containing groups such as mercapto groups.

As used herein, the terms "a" and "an" are meant to encompass both the singular and the plural forms of the thing they modify. In plural form, the thing can be the same or different. For example, "a silicone" could mean only one silicone, or it could mean more than one silicones. In the instances where more than one silicones are present, the silicones may be the same or different.

When the ingredients of the emulsions are described as being present as a weight percent, it is understood to mean that the weight of the emulsion is 100 percent and that all ingredients, including optional ingredients, will sum up to 100 weight percent. For example, an emulsion having 10 to 95 weight percent of a silicone, 0.1 to 30 weight percent of a silicone polyether and optionally water is understood to encompass any emuslion in which the amount of the silicone and silicone polyether will sum up to 100 weight percent, or the amount of silicone, silicone polyether and the optionally added water will sum up to 100 weight percent. Accordingly, when the silicone is 95 weight percent, for example, the silicone polyether can be any amount greater than 0.1 and up to 5 weight percent. In the instances when the silicone polyether is less than 5 weight percent, the optionally water is added in an amount sufficient to sum up to 100 weight percent.

Unless indicated otherwise, an "R" group refers to a monovalent organic group that may be substituted or unsubstituted. In some embodiments, R is an alkyl group containing 1 to 30 carbon atoms, alkyl having 1 to 8 carbon atoms, an alcohol having 1 to 5 carbon atoms, or an aryl having 6 to 14 carbon atoms, wherein the alkyl, alcohol, and aryl may be substituted or unsubstituted.

As used herein, "organic group" means a group containing one or more carbon atoms. An organic group comprises alkyl, alkenyl, alkynyl and aryl groups. For example, an organic group may be a group comprising from 1 to 30 carbon atoms, which group can be substituted or unsubstituted.

As used herein, "high molecular weight" when referring to silicones means silicones having a number average molecular weight of at least 100,000 g/mole.

As used herein, the term "polymer" refers to a molecule that consists of repeating monomer units that are connected to form the polymer molecule, and includes both molecules of high relative molecular mass and of low relative molecular mass. Thus, "polymer" as used in the present invention includes oligomers, homopolymers and copolymers. Copolymers include bipolymers and terpolymers.

For U.S. practice, all patent application publications and patents referenced herein, or a portion thereof if only the portion is referenced, are hereby incorporated herein by reference to the extent that the incorporated subject matter does not conflict with the present description, which would control in the case of a conflict.

Viscosity may be measured by means of any commercially available rheometer at 25° C. Suitable condition for rheology measurement known to one skilled in the art is followed. In the case when the polymer demonstrates shear thinning, zero shear viscosity is reported as the viscosity value. Values of viscosity expressed as cSt and cP are interchangeable.

As used herein, the term "water dilutable" silicone emulsion and "silicone emulsion" are used interchangeably. The "water dilutable" silicone emulsion and "silicone emulsion" refers to an emulsion to which water can be added or an emulsion that can be diluted with water. In some embodiments, water dilutable silicone emulsion is a water continuous emulsion comprising a dispersed phase and a non-dispersed (continuous) phase in which the dispersed phase is the silicone and the non-dispersed phase is water or an aqueous solution or mixture. In other embodiments, the silicone emulsion may be dilutable in non-aqueous solvents, for example, but not limited to, non-aqueous polar solvents.

In one embodiment, the present invention provides water dilutable silicone emulsions comprise a silicone gum that is a hydroxy terminated polydimethylsiloxane having a viscosity of at least 500 thousand cP at 25° C. or at least 1 million cP at 25° C.

In another embodiment, the present invention provides silicone emulsions comprise a silicone gum that is a vinyl terminated polydimethylsiloxane having a viscosity of at least 1 million cP at 25° C.

In another embodiment, the SiH functional polyorganosiloxane may have an average formula $$R_3SiO(RRSiO)_x(R^1RSiO)_ySiR_3 \quad (I)$$

wherein each R is independently an alkyl having 1 to 6 carbon atoms or an aryl having 6 to 10 carbon atoms, $R^1$ is hydrogen, x is 1 to 1000, and y is 1 to 100.

In another embodiment, the monoalkenyl functional polyoxyalkylene may be a monoalkenyl functional ethylene oxide/propylene oxide block or random copolymer. The monoalkenyl functional ethylene oxide/propylene oxide block copolymer may have an average formula $$CH_2=CH(CH_2)_n-[(C_2H_4O)_c(C_3H_6O)_d]-OR^2 \quad (II)$$

wherein $R^2$ is hydrogen or an alkyl having 1 to 12 carbon atoms; c is from 1 to 400, d is from 0 to 100, n is 0 to 10, wherein the ratio of c/(c+d) is from 0.5 to 1.

In another embodiment, the monoalkenyl functional ethylene oxide/propylene oxide block copolymer may have an average formula $$CH_2=CR^2(CH_2)_n-O[(C_2H_4O)_c(C_3H_6O)d]-R^3 \quad (IIa)$$

wherein $R^2$ is hydrogen or an alkyl having 1 to 12 carbon atoms, $R^3$ is hydrogen, alkyl or acyl, c is from 1 to 400, d is from 0 to 100, n is 0 to 10, wherein the ratio of c/(c+d) is from 0.5 to 1.

In another embodiment, the SiH functional polyorganosiloxane may have an average formula $$RRR^1SiO(RRSiO)_xSiRRR^1 \quad (III)$$

wherein each R is independently an alkyl having 1 to 6 carbon atoms or an aryl having 6 to 10 carbon atoms, $R^1$ is hydrogen, x is 1 to 1000.

In another embodiment, the dialkenyl functional polyoxyalkylene may be an dialkenyl functional ethylene oxide/propylene oxide block or random copolymer. The dialkenyl functional ethylene oxide/propylene oxide block copolymer may have an average formula $$CH_2=CR^2(CH_2)_n-O[(C_2H_4O)_c(C_3H_6O)d]$$
$$-(CH_2)_n-CR^2=CH_2 \quad (IV)$$

wherein $R^2$ is hydrogen or an alkyl having 1 to 12 carbon atoms, c is from 1 to 400, d is from 0 to 100, n is 0 to 10, wherein the ratio of c/(c+d) is from 0.5 to 1.

In another embodiment, the monoalkenyl functional polyoxyalkylene (II) may be used together with the dialkenyl functional polyoxyalkylene (IV).

In another embodiment, dialkenyl functional polyorganosiloxane is a vinyl terminal polydimethylsiloxane. The emulsions may be a water continuous emulsions. The silicone polyether component B) is water soluble or water dispersible. The water dilutable silicone emulsions may further comprise a biocide.

In another embodiment, the silicone polyether B) has a weight average molecular weight greater than 10,000 grams per mole. In another embodiment, the silicone polyether is water soluble or water dispersible. The emulsions of the present invention may be water dilutable or aqueous continuous emulsions. The emulsions of the present invention may be diluted by adding water.

In another embodiment, the present invention provides coating compositions comprising:
  A) 10-95% of the water dilutable silicone emulsion;
  B) 1 to 99 weight percent of an acrylic emulsion; or a polyurethane dispersion, or both
  C) 0 to 90 weight percent of an optional organic solvent.
The optional organic solvent in some embodiments may be a polar organic solvent.

In another embodiment, the present invention provides processes for making a silicone emulsion comprising:
  I) forming a dispersion by combining:
    A) 10 to 95 wt % of a silicone;
    B) 0.1 to 30 wt % of a silicone polyether obtainable by reacting
      i) SiH functional polyorganosiloxane,
      ii) monoalkenyl functional polyoxyalkylene,
      iii) dialkenyl functional polyorganosiloxane,
    wherein the molar ratio of SiH to alkenyl in (ii) is from 1:0.5 to 1:1.5 and the molar ratio of SiH to alkenyl in (iii) is from 1:0.01 to 1:0.5 with the proviso that the total alkenyl:SiH is from 1.5:1 to 1:1;

C) optionally a co-surfactant or co-solvent;
II) mixing and homogenizing A), B) and optionally C) from step I) to form an emulsion; and
III) optionally, adding water or other polar additives.

In another embodiment, the present invention provides processes for making a silicone emulsion comprising:
I) forming a dispersion by combining:
A) 10 to 95 wt % of a silicone having a viscosity of at least 500,000 cP at 25° C.
B) 0.1 to 30 wt % of a silicone polyether obtainable by reacting
i) SiH functional polyorganosiloxane,
ii) monoalkenyl functional polyoxyalkylene, and optionally
iii) dialkenyl functional polyorganosiloxane,
wherein the molar ratio of SiH to alkenyl in (ii) is from 1:0.5 to 1:1.5 and the molar ratio of SiH to alkenyl in (iii) is from 1:0.01 to 1:0.5 with the proviso that the molar ratio of SiH to the total combined alkenyl in (ii) and (iii) is from 1:1 to 1:1.5;
C) optionally a co-surfactant or co-solvent;
II) mixing and homogenizing A), B) and optionally C) from step I) to form an emulsion; and
III) optionally, adding water or other polar additives.

The dialkenyl functional polyorganosiloxane may be an optional component, which may be present if crosslinking is desired, or not present if crosslinking is not desired. The amount of water in step III) can be 5 to 700 parts water for every 100 parts of the step I) dispersion. The water can be added in incremental portions.

In another embodiment, the silicone polyether is obtainable by reacting
i) terminal di-SiH functional polyorganosiloxane,
ii) dialkenyl functional polyoxyalkylene,
wherein the molar ratio of SiH to alkenyl in (ii) is from 1:1 to 1:2.5;

In another embodiment, the present invention provides use of the water dilutable silicone emulsions for applying to a surface to form a coating on the surface, and use of the water dilutable silicone emulsions in a skin care product, hair care product, personal care product, household care product or automobile care product. In another embodiment the present invention is the skin care product, hair care product, personal care product, household care product or automobile care product.

The Silicone Component A)

In one embodiment, the silicone component A) is a silicone having a viscosity of at least 500,000 or at least 1,000,000 cP at 25° C. For example, silicone component A) may be a non-cyclic, straight chain or branched polyorganosiloxane containing multiple units of general formula

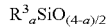

$$R^3{}_a SiO_{(4-a)/2}$$

wherein each $R^3$ may be the same or different and is an alkyl group having from 1 to 18 carbon atoms, a substituted alkyl group having from 1 to 18 carbon atoms, a aryl group having up to 12 carbon atoms, or a substituted aryl group having up to 12 carbon atoms, and a is 1, 2 or 3. The polyorganosiloxane may be a hydroxy terminated polyorganosiloxane, or polydimethylsiloxane.

In one embodiment, the silicone component A) has a viscosity, at 25° C., of from 500,000 cP to 50,000,000 cP at 25° C., alternatively from 500,000 cP to 40,000,000 cP, alternatively from 500,000 cP to 30,000,000 cP, alternatively from 500,000 cP to 20,000,000 cP, alternatively from 500,000 cP to 10,000,000 cP or alternatively from 500,000 cP to 1,000,000 cP.

In another embodiment, the silicone component A) can be a silicone gum, a silicone resin, a silicone pressure sensitive adhesive (PSA), an aminofunctional organopolysiloxane, a phenylated silicone, a carboxylated silicone, hydroxy terminated silicone, vinyl terminated silicone, a silicone fluid, or any combination thereof. The silicone component A) is not an antifoam.

In one embodiment, the silicone component A) is a silicone gum. As used herein, "silicone gum" refers to predominately linear organopolysiloxanes having sufficiently high molecular weight to provide kinematic viscosities greater than 500 thousand cSt at 25° C. For example, the formula molecular weight can be about 250,000. While any organopolysiloxane considered as a gum may be selected as component A), typically the silicone gum is a diorganopolysiloxane gum with a molecular weight sufficient to impart a William's plasticity number of at least about 30 as determined by the American Society for Testing and Materials (ASTM) test method 926. The silicon-bonded organic groups of the diorganopolysiloxane may be substituted. For example, the organic groups may be independently selected from alkyl or halogenated alkyl groups. In one embodiment, the organic groups may be exemplified by alkyl groups having 1 to 20 carbon atoms, such as methyl, ethyl, propyl, butyl, pentyl and hexyl; cycloalkyl groups, such as cyclohexyl and cycloheptyl; aryl groups having 6 to 12 carbon atoms, such as phenyl, tolyl and xylyl; aralkyl groups having 7 to 20 carbon atoms, such as benzyl and phenylethyl; and halogenated alkyl groups having 1 to 20 carbon atoms, such as 3,3,3-trifluoropropyl and chloromethyl.

In another embodiment, the diorganopolysiloxane can be a homopolymer, a copolymer or a terpolymer containing such organic groups. Examples include, but are not limited to, homopolymers comprising dimethylsiloxy units, homopolymers comprising 3,3,3-trifluoropropylmethylsiloxy units, copolymers comprising dimethylsiloxy units and phenylmethylsiloxy units, copolymers comprising dimethylsiloxy units and 3,3,3-trifluoropropylmethylsiloxy units, copolymers of dimethylsiloxy units and diphenylsiloxy units and terpolymers of dimethylsiloxy units, diphenylsiloxy units and phenylmethylsiloxy units.

The silicon-bonded organic groups of the diorganopolysiloxane may be selected from alkenyl groups having 1 to 20 carbon atoms, such as, but not limited to, vinyl, allyl, butenyl, pentenyl, hexenyl, or dodecenyl. Examples include dimethylvinylsiloxy-endblocked dimethylpolysiloxanes; dimethylvinylsiloxy-endblocked dimethylsiloxane-methylvinylsiloxane copolymers; dimethylvinylsiloxy-endblocked methylphenylpolysiloxanes; and dimethylvinylsiloxy-endblocked methylphenylsiloxane-dimethylsiloxane-methylvinylsiloxane copolymers.

The silicon-bonded organic groups of the diorganopolysiloxane may also be selected from various organofunctional groups such as amino, amido, mercapto, or epoxy functional groups.

The molecular structure of the diorganopolysiloxane may be exemplified by straight-chain (linear) unbranched structures and by partially branched straight-chain structures. In some embodiments, straight-chain (unbranched) structures are preferred.

In one embodiment, the silicone component A) can be any one of the above-described silicone gum or any combination thereof. In another embodiment, the silicone gum is a hydroxy terminated polydimethylsiloxane gum having a viscosity of at least 20 million cP at 25° C.

The silicone gum may be used in combination with other organopolysiloxanes. Organopolysiloxanes are polymers containing siloxane units independently selected from $(R_3SiO_{1/2})$, $(R_2SiO_{2/2})$, $(RSiO_{3/2})$, or $(SiO_{4/2})$ siloxy units, where R may be any monovalent organic group. When R is a methyl group in the $(R_3SiO_{1/2})$, $(R_2SiO_{2/2})$, $(RSiO_{3/2})$, or $(SiO_{4/2})$ siloxy units of an organopolysiloxane are commonly referred to as M, D, T, and Q units, respectively. These siloxy units can be combined in various manners to form cyclic, linear, or branched structures. The chemical and physical properties of the resulting polymeric structures can vary. For example organopolysiloxanes can be volatile or low viscosity fluids, high viscosity fluids (or gums), elastomers or rubbers, and resins depending on the number and type of siloxy units in the average polymeric formula. The R groups may be any monovalent organic group, alternatively R is an alkyl group containing 1 to 30 carbons, or alternatively R is methyl.

The amount of the other organopolysiloxane combined with the silicone gum may vary. Typically, 0.1 parts to 1000 parts by weight, alternatively 0.1 to 100 parts by weight of the other organopolysiloxane is added for every 100 parts of the silicone gum.

In one embodiment, the silicone component A) is an aminofunctional organopolysiloxane. As used herein, "aminofunctional organopolysiloxanes" may be characterized by having at least one of the R groups in the formula $R_mSiO_{(4-m)/2}$ be an aminofunctional group wherein m is 1, 2 or 3. The amino-functional group may be present on any siloxy unit having an R substituent, that is, they may be present on any $(R_3SiO_{1/2})$, $(R_2SiO_{2/2})$ or $(RSiO_{3/2})$ unit, and is designated in the formula herein as $R^N$. The aminofunctional group $R^N$ may be illustrated by groups having the formula: $-R^4NHR^5$, $-R^4NR^5{}_2$, or $-R^4NHR^4NHR^5$, wherein each $R^4$ is independently a divalent alkyl group (alkylene) having 1 to 20 carbon atoms, and each $R^5$ is independently hydrogen or an alkyl group 1 to 20 carbon atoms. Each $R^4$ is typically an alkylene group having from 2 to 20 carbon atoms, and is illustrated by groups such as, but not limited to, $-CH_2CH_2-$, $-CH_2CH_2CH_2-$, $-CH_2CHCH_3-$, $-CH_2CH_2CH_2CH_2-$, $-CH_2CH(CH_3)CH_2-$, $-CH_2CH_2CH_2CH_2CH_2-$, $-CH_2CH_2CH_2CH_2CH_2CH_2-$, $-CH_2CH_2CH(CH_3CH_3)CH_2CH_2CH_2-$, $-CH_2CH_2CH_2CH_2CH_2CH_2CH_2CH_2-$, and $-CH_2CH_2CH_2CH_2CH_2CH_2CH_2CH_2CH_2-$. The alkyl groups of $R^5$ are as illustrated above for R.

Non-limiting examples of amino-functional group $R^N$ are $-CH_2CH_2NH_2$, $-CH_2CH_2CH_2NH_2$, $-CH_2CH(CH_3)NH_2$, $-CH_2CH_2CH_2CH_2NH_2$, $-CH_2CH_2CH_2CH_2CH_2NH_2$, $-CH_2CH_2CH_2CH_2CH_2CH_2NH_2$, $-CH_2CH_2NHCH_3$, $-CH_2CH_2CH_2NHCH_3$, $-CH_2CH(CH_3)CH_2NHCH_3$, $-CH_2CH_2CH_2CH_2NHCH_3$, $-CH_2CH_2NHCH_2CH_2NH_2$, $-CH_2CH_2CH_2NHCH_2CH_2NH_2$, $-CH_2CH_2CH_2CH_2NHCH_2CH_2CH_2NH_2$, $-CH_2CH_2CH_2CH_2NHCH_2 CH_2CH_2NH_2$, $-CH_2CH_2NHCH_2CH_2NHCH_3$, $-CH_2CH_2CH_2NHCH_2CH_2NHCH_3$, $-CH_2CH_2CH_2CH_2 NHCH_2CH_2CH_2NHCH_3$, and $-CH_2CH_2NHCH_2 CH_2NHCH_2CH_2CH_2CH_3$.

Alternatively, the amino functional group $R^N$ may be $-CH_2CH(CH_3)CH_2NHCH_2CH_2NH_2$.

In one embodiment, the aminofunctional organopolysiloxane may have the average formula:

$[R_3SiO_{1/2}][R_2SiO_{2/2}]_e[RR^NSiO_{2/2}]_f[R_3SiO_{1/2}]$ wherein:
e is 1-1000, alternatively 1 to 500, alternatively 1 to 200;
f is 1-100, alternatively 1 to 50, alternatively 1 to 10;
R is independently a monovalent organic group, alternatively R is an alkyl containing 1 to 30 carbon atoms,
alternatively R is an alkyl group containing 1 to 12 carbons, or alternatively R is a methyl group; and
$R^N$ is as defined above.

The silicone component A) can be any one of the above-described aminofunctional organopolysiloxane or any combination thereof.

In another embodiment, the silicone component A) is a silicone resin. As used herein, "silicone resin" refers to any organopolysiloxane containing at least one $(RSiO_{3/2})$ or $(SiO_{4/2})$ siloxy unit. Silicone resin organopolysiloxanes result when a majority of the siloxy units are selected from T or Q siloxy units. When an organopolysiloxane mostly contains T siloxy units, it is often referred to as a "silsesquioxane resin". When M and Q siloxy units predominate, the resulting organosiloxane is often referred to as a "MQ resin". Alternatively, the formula for an organopolysiloxane may be designated by the average of the siloxy units in the organopolysiloxane as follows; $R_mSiO_{(4-m)/2}$, where the R is independently an organic group, alternatively an alkyl, or alternatively methyl. The value of m in the average formula may be used to characterize the organopolysiloxane. For example, an average value of m=1 would indicate a predominate concentration of the $(RSiO_{3/2})$ siloxy unit in the organopolysiloxane, while m=2 would indicate a predominance of $(R_2SiO_{2/2})$ siloxy units. Accordingly, a silicone resin refers to those organopolysiloxanes having a value of m less than 1.8 in the average formula $R_mSiO_{(4-m)/2}$.

The silicone resin useful as the silicone component A) may independently comprise (i) $(R_3SiO_{1/2})_g$, (ii) $(R_2SiO_{2/2})_h$, (iii) $(RSiO_{3/2})_i$, and (iv) $(SiO_{4/2})_j$ siloxy units, providing there is at least one T or Q siloxy unit in the silicone resin molecule. The amount of each unit present in the silicone resin is expressed as a mole fraction (i.e., g, h, i, or j) of the total number of moles of all M, D, T, and Q units present in the silicone resin. Any such formula used herein to represent the silicone resin does not indicate structural ordering of the various siloxy units. Rather, such formulae are meant to provide a convenient notation to describe the relative amounts of the siloxy units in the silicone resin, as per the mole fractions described above via the subscripts g, h, i, and j.

The silicone resin may also contain silanol groups (hydroxy bonded to a silicon atom). The amount of silanol groups present on the silicone resin may vary from 0.1 to 35 mole percent silanol groups [≡SiOH], alternatively from 2 to 30 mole percent silanol groups [≡SiOH], alternatively from 5 to 20 mole percent silanol groups [≡SiOH]. The silanol groups may be present on any siloxy units within the silicone resin. The mole fractions of the various siloxy units and silanol content may be readily determined by $^{29}Si$ NMR techniques.

The molecular weight of the silicone resin is not limited. The silicone resin may have a $M_n$ (number average molecular weight) of at least 1,000 g/mole, alternatively $M_n$ of at least 2,000 g/mole, or alternatively $M_n$ of at least 5,000 g/mole. The number average molecular weight may be readily determined using Gel Permeation Chromatography (GPC) techniques.

In one embodiment, the silicone resin is a MQ silicone. The silicone resin may be a MQ resin comprising at least 80 mole % of siloxy units selected from $(R_3SiO_{1/2})_g$ and $(SiO_{4/2})_j$ units (that is g+j≥0.8), where R is an alkyl group having from 1 to 8 carbon atoms, an aryl group, a hydroxy containing group, or an amino group, with the proviso that at least 95 mole % of the R groups are alkyl groups, a and d each have a value greater than zero, and the ratio of a/d is 0.5 to 1.5.

The R groups of the MQ resin are independently an alkyl group having from 1 to 8 carbon atoms, an aryl group, a carbinol group, or an amino group. The alkyl groups are illustrated by methyl, ethyl, propyl, butyl, pentyl, hexyl, and octyl. The aryl groups are illustrated by phenyl, naphthyl, benzyl, tolyl, xylyl, biphenyl, methylphenyl, 2-phenylethyl, 2-phenyl-2-methylethyl, chlorophenyl, bromophenyl and fluorophenyl with the aryl group typically being phenyl.

MQ resins suitable for use as component (A), and methods for their preparation, are known in the art. For example, U.S. Pat. No. 2,814,601 discloses that MQ resins can be prepared by converting a water-soluble silicate into a silicic acid monomer or silicic acid oligomer using an acid. When adequate polymerization has been achieved, the resin is end-capped with trimethylchlorosilane to yield the MQ resin. Another method for preparing MQ resins is disclosed in U.S. Pat. No. 2,857,356 that discloses a method for the preparation of an MQ resin by the co-hydrolysis of a mixture of an alkyl silicate and a hydrolyzable trialkylsilane organopolysiloxane with water.

The MQ resins suitable as the silicone component A) in the present invention may contain D and T units. The MQ resins may also contain hydroxy groups. Typically, the MQ resins have a total weight percent of hydroxy content of 2-10 weight percent, alternatively 2-5 weight percent. The MQ resins can also be further "capped" wherein residual hydroxy groups are reacted with additional M groups. Hydroxy content is determined by $^{29}$Si NMR techniques.

In one embodiment, the silicone resin is a silsesquioxane resin. The silsesquioxane resin may be a silsesquioxane resin comprising at least 80 mole percent of $RSiO_{3/2}$ units, wherein R is independently an alkyl group of 1 to 20 carbon atoms, a methanol or substituted methanol radical, or an alkyl group of 1 to 20 carbon atoms having an amino substituent. The alkyl group may include halogen substituted alkyl. The R group may be an aryl group, such as phenyl, naphthyl, and anthryl groups. Alternatively, R may be an alkyl group, such as methyl, ethyl, propyl, or butyl. Alternatively, R may be any combination of the aforementioned alkyl or aryl groups. Alternatively, R is phenyl, propyl, or methyl. In one embodiment, at least 40 mole % of the R groups are propyl, referred herein as T-propyl resins, since the majority of the siloxane units are T units of the general formula $RSiO_{3/2}$ where at least 40 mole %, alternatively 50 mole %, or alternatively 90 mole % of the R groups are propyl. In another embodiment, at least 40 mole % of the R groups are phenyl, referred herein as T-phenyl resins, since the majority of the siloxane units are T units of the general formula $RSiO_{3/2}$ where at least 40 mole %, alternatively 50 mole %, or alternatively 90 mole % of the R groups are phenyl. In yet another embodiment, R may be a mixture of propyl and phenyl. When R is a mixture of propyl and phenyl, the amounts of each in the resin may vary, but typically the R groups in the silsesquioxane resin may contain 60-80 mole percent phenyl and 20-40 mole percent propyl.

Silsesquioxane resins are known in the art and are typically prepared by hydrolyzing an organosilane having three hydrolyzable groups on the silicon atom, such as a halogen or alkoxy group. Thus, silsesquioxane resins can be obtained by hydrolyzing propyltrimethoxysilane, propyltriethoxysilane, propyltripropoxysilane, or by co-hydrolyzing the aforementioned propylalkoxysilanes with various alkoxysilanes. Examples of these alkoxysilanes include methyltrimethoxysilane, methyltriethoxysilane, methyltriisopropoxysilane, dimethyldimethoxysilane, and phenyltrimethoxysilane. Propyltrichlorosilane can also be hydrolyzed alone, or in the presence of alcohol. In this case, co-hydrolyzation can be carried out by adding methyltrichlorosilane, dimethyldichlorosilane, phenyltrichlorosilane, or similar chlorosilanes and methyltrimethoxysilane, methyltriethoxysilane, methyltriisopropoxysilane, or similar methylalkoxysilane. Alcohols suitable for these purposes include methanol, ethanol, n-propyl alcohol, isopropyl alcohol, butanol, methoxy ethanol, ethoxy ethanol, or similar alcohols. Examples of hydrocarbon-type solvents which can also be concurrently used include toluene, xylene, or similar aromatic hydrocarbons; hexane, heptane, isooctane, or similar linear or partially branched saturated hydrocarbons; and cyclohexane, or similar aliphatic hydrocarbons.

In one embodiment, the silsesquioxane resins may contain M, D, and Q units, but typically at least 80 mole percent, alternatively 90 mole percent of the total siloxane units are T units. The silsesquioxane resins may also contain hydroxy and/or alkoxy groups. Typically, the silsesquioxane resins have a total weight percent of hydroxy content of 2-10 weight percent and a total weight percent of alkoxy content of up to 20 weight percent, alternatively 6-8 weight percent of hydroxy content and up to 10 weight percent of alkoxy content.

Representative, non-limiting examples of commercial silicone resins suitable as silicone component A) include silicone resins sold under the trademarks DOW CORNING® 840 Resin, DOW CORNING® 2-7466 Resin, DOW CORNING® 2-9138 Resin, DOW CORNING® 2-9148 Resin, DOW CORNING® 2104 Resin, DOW CORNING® 2106 Resin, DOW CORNING® 217 Flake Resin, DOW CORNING® 220 Flake Resin, DOW CORNING® 233 Flake Resin, DOW CORNING® 4-2136 Resin, Xiameter® RSN-6018 Resin, Xiameter® RSN-0217 Resin, Silres® MK methyl silicone resin, and Dow Corning® MQ 1600 Resin.

Silicone resin also encompasses silicone-organic resins. Silicone-organic resins include silicone-organic copolymers, where the silicone portion contains at least one $(RSiO_{3/2})$, or $(SiO_{4/2})$ siloxy unit. The silicone portion of the silicone-organic resin may be any of the silsesquioxane or MQ resins as described above. The organic portion may be any organic polymer, such as those derived by free radical polymerization of one or more ethylenically unsaturated organic monomers. Various types of ethylenically unsaturated and/or vinyl containing organic monomers can be used to prepare the organic portion including; acrylates, methacrylates, substituted acrylates, substituted methacrylates, vinyl halides, fluorinated acrylates, and fluorinated methacrylates, for example. Some representative compositions include acrylate esters and methacrylate esters such as methyl acrylate, ethyl acrylate, butyl acrylate, 2-ethylhexyl acrylate, methyl methacrylate, decyl acrylate, lauryl acrylate, isodecyl methacrylate, lauryl methacrylate, and butyl methacrylate; substituted acrylates and methacrylates such as hydroxyethyl acrylate, perfluorooctyl acrylate, hydroxypropyl acrylate, hydroxypropyl methacrylate, and hydroxyethyl methacrylate; vinyl halides such as vinyl chloride, vinylidene chloride, and chloroprene; vinyl esters such as vinyl acetate and vinyl butyrate; vinyl pyrrolidone; conjugated dienes such as butadiene and isoprene; vinyl aromatic compounds such as styrene and divinyl benzene; vinyl monomers such as ethylene; acrylonitrile and methacrylonitrile; acrylamide, methacrylamide, and N-methylol acrylamide; and vinyl esters of monocarboxylic acids.

The silicone component A) can be any one of the above-described silicone resin or any combination of the above-described silicone resins.

In another embodiment, the silicone component A) is a pressure sensitive adhesive (PSA). A PSA refers to the reaction products resulting from reacting a hydroxyl endblocked linear organopolysiloxane with a resin organopolysiloxane, wherein the resin organopolysiloxane contains at least one ($RSiO_{3/2}$) or ($SiO_{4/2}$) siloxy unit. When silicone component A) is a PSA, it may be the reaction product of a hydroxy endblocked polydimethylsiloxane polymer and a hydroxy functional silicate or silicone resin. Typically, the hydroxy functional silicate resin is a trimethylsiloxy and hydroxy endblocked silicate resin, such as the silicone resins described above. The polydimethylsiloxane polymer and hydroxy functional silicate resin are reacted in a condensation reaction to form the silicone PSA.

PSA's are disclosed in U.S. Pat. Nos. 4,584,355; 4,585,836; 4,591,622; 5,726,256; 5,776,614; 5,861,472; 5,869,556; and 6,337,086 which are suitable PSA's for silicone component A). The PSA as silicone component A) may also be a silicone acrylate hybrid composition as disclosed in WO2007/145996.

Representative, non-limiting examples of commercially available PSA's suitable as component A) include; Dow Corning® Q2-7406 Adhesive, Dow Corning® Q2-7735 Adhesive, Dow Corning® 7355 Adhesive, Dow Corning® 7358 Adhesive, Dow Corning® Q2-7566 Adhesive, Dow Corning® 7-4100 Adhesive, Dow Corning® 7-4200 Adhesive, Dow Corning® 7-4300 Adhesive, Dow Corning® 7-4400 Adhesive, Dow Corning® 7-4500 Adhesive, Dow Corning® 7-4600 Adhesive, Dow Corning® 7-4560, Shin-Etsu KR-100, Shin-Etsu KR-101-10, Shin-Etsu SR-130 Momentive PSA518, Momentive SPUR+ PSA 3.0, Momentive SILGRIP PSA529, Momentive SILGRIP PSA915, Momentive SILGRIP PSA610, Momentive SILGRIP PSA595, Momentive SILGRIP PSA6374, and Momentive SILGRIP PSA6574.

In another embodiment, the silicone component A) may be a carboxylated organopolysiloxane, phenylated organopolysiloxane, OH terminal organopolysiloxane, vinyl functional organopolysiloxane, or any combination thereof.

The Silicone Polyether Component B)

In one embodiment, the silicone polyether component B) may be a polydiorganosiloxane-polyoxyalkylene copolymer containing at least one polydiorganosiloxane segment and at least one polyoxyalkylene segment. The polyoxyalkylene segments may be bonded to the polydiorganosiloxane segments with silicon-oxygen-carbon bonds and/or with silicon-carbon bonds. The polydiorganosiloxane segments of the polydiorganosiloxane-polyoxyalkylene copolymer consist essentially of siloxane units which are interlinked by Si—O—Si linkages and which have the general formula

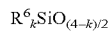

wherein k is 0, 1, 2 or 3, $R^6$ is independently methyl, ethyl, vinyl, phenyl, or divalent group bonding a polyoxyalkylene segment to the polydiorganosiloxane segment. The siloxane units may be arranged in such a way as to produce linear or branched polydiorganosiloxane segments, and the linear or branched polydiorganosiloxane segments may be non-crosslinked or crosslinked.

The number average molecular weight of the polydiorganosiloxane having one or more polyoxyalkylene segments is 1000 to 2,000,000.

The polydiorganosiloxane-polyoxyalkylene copolymer may be in a block arrangement of segments such as $(AB)_p$, $A(BA)_p$ and $B(AB)_p$ or a pendant arrangement of segments such as $(AB_q)_p$ or combinations thereof, wherein A denotes a polyoxyalkylene segment, B denotes a polydiorganosiloxane and p and q denote integers greater than zero and greater than one, respectively.

In another embodiment, the silicone polyether component B) is obtainable by reacting
i) SiH functional polyorganosiloxane,
ii) monoalkenyl functional polyoxyalkylene,
iii) dialkenyl functional polyorganosiloxane,
wherein the molar ratio of SiH to alkenyl in (ii) is from 1:1 to 30:1) and the molar ratio of SiH to alkenyl in (iii) is from 1:0.01 to 1:1 with the proviso that the total alkenyl:SiH is from 1.5:1 to 1:1.

The polydiorganosiloxane-polyoxyalkylene copolymer may be in a block arrangement of segments such as $A(BA)_p$ or a pendant arrangement of segments such as $B[A]_q$ or combinations thereof, wherein A denotes a polyoxyalkylene segment, B denotes a polydiorganosiloxane and p and q denote integers greater than zero, and the bracket designates a pendant position.

In another embodiment, the silicone polyether component B) is obtainable by reacting
i) SiH functional polyorganosiloxane,
ii) monoalkenyl functional polyoxyalkylene, and optionally iii) dialkenyl functional polyorganosiloxane,
wherein the molar ratio of SiH to alkenyl in (ii) is from 1:0.5 to 1:1.5 and the molar ratio of SiH to alkenyl in (iii) is from 1:0.01 to 1:0.5 with the proviso that the molar ratio of SiH to the total combined alkenyl in (ii) and (iii) is from 1:1 to 1:1.5.

The silicone polyether component B) is either a linear or a crosslinked organopolysiloxane polymer having at least one polyoxyalkylene group. Compounds suitable as component B) include organopolysiloxane polymer molecules having at least polyoxyalkylene group that is terminal or pendant to the organopolysiloxane, and that are cross-linked through a cross-linking agent that is an organopolysiloxane.

The silicone polyether component B) may be obtained by a method comprising preparing a linear or cross-linked organopolysiloxane polymer and combining a polyoxyalkylene group therewith, or by a method comprising preparing a linear organopolysiloxane having a polyoxyalkylene group, and optionally cross-linking the organopolysiloxane.

The crosslinking of the organopolysiloxane can be done by methods those skilled in the art will readily recognize. For example, the skilled person would be able to know what starting materials are mutually compatible to carry out the method of preparing the silicone polyether component B).

When cross linked organopolysiloxane in B) is desired, the crosslinking may be obtained by the addition reaction between the following components: an polyorganosiloxane having at least two Si—H groups in the side chains of each molecule and a polyorganosiloxane having each of its terminals blocked with an alkenyl group. Alternatively, the crosslinking may be obtained by addition reaction between an polyorganosiloxane having an Si—H group at each of its terminals and an polyorganosiloxane having at least two alkenyl groups in the side chains of each molecule thereof. In one embodiment, the polyorganosiloxane having the alkenyl groups may be a vinyl terminated polyorganosiloxane.

In another embodiment, the silicone polyether component B) is obtainable by reacting
i) terminal di-SiH functional polyorganosiloxane,
ii) dialkenyl functional polyoxyalkylene,
wherein the molar ratio of SiH to alkenyl in (ii) is from 1:1 to 1:2.5.

The polyorganosiloxane having the alkenyl groups bridges the polyorganosiloxane having Si—H groups (the polyorganosiloxane backbone) and does not contain any reactive sites for addition of polyoxyalkylene moieties. The polyorganosiloxane bridge and polyorganosiloxane backbone create a siloxane network at the interface of water and the silicone component A).

The exact number of organopolysiloxane-polyoxyalkylene polymer molecules which will be bridged together will vary within each compound of the silicone polyether component B). One limitation on the cross-linking is that the overall molecular weight does not cause the material to gel. In one embodiment, the molecular weight of silicone polyether component B) can be 5000 to 2,000,000 based on the formula molecular weight, or alternatively in the range of 20,000 to 100,000. In another embodiment, the silicone polyether component B) can have viscosity of 100 to 100,000 mm$^2$/s at 25° C. In still another embodiment, the silicone polyether component B) has a weight average molecular weight greater than 10,000 grams per mole.

The polyoxyalkylene units in the monoalkenyl or dialkenyl functional polyoxyalkylene comprise polyoxyethylene (EO), polyoxypropylene (PO) or any combination thereof. In one embodiment, the silicone polyether component B) comprises from 1 to 400 EO units or 1 to 100 EO units. I another embodiment, the silicone polyether component B) comprises 0 to 100 PO units, or 1 to 50 PO units. In another embodiment, silicone polyether component B) comprises 1 to 150 EO units and 0 to 100 PO units, or 1 to 100 EO units and 1 to 50 PO units.

In one embodiment, the silicone polyether component B) may be prepared by a method comprising steps: (I) a charging step in which a linear polysiloxane having hydrogen atoms in its side chains, a polyorganosiloxane having aliphatic unsaturated groups and a catalyst for promoting the reaction, particularly platinum catalysts such as an isopropanol solution of H$_2$PtCl$_6$H$_2$O with a 2% methanol solution of sodium acetate are placed in a reactor, (II) an agitation/heating step in which agitation is conducted, for example, at 40° C. for 30 minutes, (III) an input step in which a polyoxyalkylene having an aliphatic unsaturated group and a solvent (isopropanol) are put in the reactor, (IV) a reflux step in which the isopropanol is refluxed, for example, at 80° C. for 1.5 to 2 hours while monitoring the reaction rate of EO, (V) a stripping step in which the isopropanol is stripped, for example, at 130° C. under a reduced pressure of 25 mmHg, and (VI) a final step in which the reduced pressure condition of step (V) is released and the reaction mixture is cooled to 60° C. to obtain a final product.

In one embodiment, the molar ratio of the SiH units to the aliphatic unsaturated groups of the polyorganosiloxane component may range from 1:0.001 to 1:0.2 or 1:0.01 to 1:0.5. The molar ratio of the SiH units to the aliphatic unsaturated group of the polyoxyalkylene component may range from 1:0.01 to 1:1 or 1:1.5 to 30:1, with the proviso that the ratio of the total aliphatic unsaturated groups to the SiH is from 1.5:1 to 1:1 or from 2.5:1 to 1:1.

Typically, the amounts of the aliphatic unsaturated groups is molar excess to the SiH groups.

The hydrosilylation catalyst may be any suitable metal based catalyst selected from a platinum, rhodium, iridium, palladium or ruthenium. Group VIII group metal containing catalysts useful to catalyze curing of the present compositions can be any of those known to catalyze reactions of silicon bonded hydrogen atoms with silicon bonded unsaturated hydrocarbon groups. The preferred Group VIII metal for use as a catalyst to effect cure of the present compositions by hydrosilylation is a platinum based catalyst. Some preferred platinum based hydrosilylation catalysts for curing the present composition are platinum metal, platinum compounds and platinum complexes.

Suitable platinum catalysts are described in U.S. Pat. No. 2,823,218 (commonly referred to as "Speier's catalyst) and U.S. Pat. No. 3,923,705. The platinum catalyst may be "Karstedt's catalyst", which is described in Karstedt's U.S. Pat. Nos. 3,715,334 and 3,814,730. Karstedt's catalyst is a platinum divinyl tetramethyl disiloxane complex typically containing about one-weight percent of platinum in a solvent such as toluene. Alternatively the platinum catalyst may be a reaction product of chloroplatinic acid and an organosilicon compound containing terminal unsaturated aliphatic, as described in U.S. Pat. No. 3,419,593. Alternatively, the hydrosilylation catalyst is a neutralized complex of platinum chloride and divinyl tetramethyl disiloxane, as described in U.S. Pat. No. 5,175,325. Further suitable hydrosilylation catalysts are described in, for example, U.S. Pat. Nos. 3,159,601; 3,220,972; 3,296,291; 3,516,946; 3,989,668; 4,784,879; 5,036,117; 5,175,325 and EP0347895B1.

The hydrosilylation catalyst may be added in an amount equivalent to as little as 0.001 part by weight of elemental platinum group metal, per one million parts (ppm) of the total reaction composition. Typically, the concentration of the hydrosilylation catalyst in the reaction composition is that capable of providing the equivalent of at least 1 part per million of elemental platinum group metal. A catalyst concentration providing the equivalent of 1 to 500, alternatively 50 to 500, alternatively 50 to 200 parts per million of elemental platinum group metal may be used.

The hydrosilylation reaction is an addition reaction in which the SiH units react with the aliphatic unsaturated group to form an Si—C bond. The reaction may be conducted under those conditions known in the art for effecting hydrosilylations reactions.

The hydrosilylation reaction can be conducted neat or in the presence of a solvent. The solvent can be an alcohol such as methanol, ethanol, isopropanol, butanol, n-propanol, or branched Guerbet alcohols, a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether; a halogenated hydrocarbon such as dichloromethane, 1,1,1-trichloroethane, methylene chloride, or chloroform; dimethyl sulfoxide, dimethyl formamide, acetonitrile, tetrahydrofuran, white spirits, mineral spirits, naphtha, or any combination thereof.

The amount of solvent can be up to 70 weight percent, but is typically from 20 to 50 weight percent, said weight percent being based on the total weight of components in the hydrosilylation reaction. The solvent used during the hydrosilylation reaction can be subsequently removed from the resulting silicone polyether by various known methods. Additional components can be added to the hydrosilylation reaction which are known to enhance such reactions. These components include salts such as sodium acetate which have a buffering effect in combination with platinum catalysts.

The silicone polyether component B) of the present invention comprises a polyoxyalkylene groups which can be polyoxyethylene (EO) designated by $(C_2H_4O)_r$, wherein r is from 1 to 500. The polyoxyalkylene group may also contain oxypropylene (PO) units designated by $(C_3H_6O)_s$ wherein s is form 0 to 100, oxybutylene units $(C_4H_8O)_t$ wherein t is from 0 to 50, or mixtures thereof. When the polyoxyalkylene group comprises a mixture of $(C_2H_4O)$, $(C_3H_6O)$, and/or $(C_4H_8O)$ units, the oxyalkylene groups are typically randomized, but can also be blocked. The content of the EO and/or PO in the silicone polyether component B) is such that the silicone polyether is water soluble or water dispersable.

The polyoxyalkylene groups are added to the SiH functional polyorganosiloxane from any polyoxyalkylene that is terminated at one molecular chain end with an unsaturated aliphatic hydrocarbon group (monofunctional) containing 2 to 12 carbon atoms. The polyoxyalkylene may result from the polymerization of ethylene oxide, propylene oxide, butylene oxide, 1,2-epoxyhexane, 1,2-epoxyoctance, cyclic epoxides such as cyclohexene oxide or exo-2,3-epoxynorborane. The polyoxyalkylene group may comprise predominately oxyethylene units, but may also contain oxypropylene units, oxybutylene units, or mixtures thereof. The unsaturated aliphatic hydrocarbon group can be an alkenyl or alkynyl group. Representative, non-limiting examples of the alkenyl groups are shown by the following structures $H_2C=CH-$, $H_2C=CHCH_2-$, $H_2C=CHC(CH_3)_2-$, $H_2C=C(CH_3)CH_2-$, $H_2C=CHCH_2CH_2-$, $H_2C=CHCH_2CH_2CH_2-$, and $H_2C=CHCH_2CH_2CH_2CH_2-$. Representative, non-limiting examples of alkynyl groups are shown by the following structures: $HC\equiv C-$, $HC\equiv CCH_2-$, $HC\equiv CCH(CH_3)-$, $HC\equiv CC(CH_3)_2-$, and $HC\equiv CC(CH_3)_2CH_2-$.

The silicone polyether component B) water is soluble or water dispersable.

The present invention provides for the emulsification of silicone gums (or silicone of very high viscosity) and the use of the resultant emulsions in coating applications. In particular, the emulsions can be used in applications where there are coalescing agents or solvents. Such coalescing agents or solvents may be, for example, polar to weakly polar solvents such as alcohols and glycol ethers. In one embodiment, the emulsions of the present invention may have or may be used in applications having from 0.5 to 5% by weight of a coalescing agent.

In one embodiment, the silicone polyether may be a rake-type (graft-type) silicone polyether. Such rake-type silicone polyethers may be obtainable by reacting
   i) an SiH-functional polyorganosiloxane of formula (I) and
   ii) a monoalkenyl-functional polyoxyalkylene of formula (II)

The alkenyl:SiH ratio should be 1.5 to 1:1. In another embodiment, the silicone polyether is an A(BA)p where p is an integer greater than zero, A is a polyoxyalkylene and B is a polyorganosiloxane. Examples of such silicone polyether include ABA and ABAB . . . BA. Such silicone polyether may be obtainable by a reaction of
   i) an SiH-functional polyorganosiloxane of formula (III);
   ii) a dialkenyl-functional polyoxyalkylene of formula (IV)
wherein the SiH groups are at the terminal positions, and the molar ratio of SiH to alkenyl is from 1:2.5 to 1:1.

In one embodiment, the emulsions of the present invention provide for the use of silicone polyethers having very high molecular weights, for example, greater than 1,0,000 grams per mole.

In another embodiment, the emulsions of the present invention provide for the use of silicone polyethers in which the silicone:polyether and EO:PO ratios can be varied to tune the properties of the silicone polyether to accommodate a range of applications.

Any solvent used in preparing the silicone polyethers may be removed or retained in the final product where it will act to lower the viscosity, facilitating synthesis and also final handling. In the cases where the solvent is retained, it can be a solvent useful for the final application. A reaction solvent may also be exchanged for another useful solvent subsequent to reaction. Examples of solvent retained or exchanged for in the final product include glycols, ethers and polycondensation products thereof. The solvent may also be a surface active agent.

In some embodiments, the emulsions comprise a co-surfactant and may be present such that the weight ratio of the co-surfactant to the silicone polyether B) is no greater than 5. In other embodiments, the emulsions comprise a co-solvent, where weight ratio of co-solvent to the silicone polyether B) is no greater than 5. In another embodiment, the emulsions comprise a co-surfactant and a co-solvent, wherein the ratio of the combined weight of the co-surfactant and co-solvent to the silicone polyether B) is no greater than 5. In some embodiments, the co-solvent may be a non-aqueous polar co-solvent In one embodiment, the present invention provides a process for making a silicone emulsion comprising: I) forming a dispersion by combining: A) 10 to 95 wt % of a silicone; B) 0.1 to 30 wt % of a silicone polyether obtainable by reacting i) SiH functional polyorganosiloxane, ii) monoalkenyl functional polyoxyalkylene, iii) dialkenyl functional polyorganosiloxane, wherein the molar ratio of SiH to alkenyl in (ii) is from 1:1 to 30:1 and the molar ratio of SiH to alkenyl in (iii) is from 1:0.01 to 1:1 with the proviso that the total alkenyl:SiH is from 1.5:1 to 1:1; C) optionally a co-surfactant or co-solvent; II) mixing and homogenizing A), B) and optionally C) from step I) to form an emulsion; and III) optionally, add water or other polar additives.

In one embodiment, the dispersion formed in step I) consists essentially of components A) and B). In this embodiment, the dispersion is essentially free of additional co-surfactants or co-solvents are added in step I). As used herein, the phrase "essentially free of" co-solvents means that co-solvents are not added to components A) and B) in order to create a mixture of suitable viscosity that can be processed on typical emulsification devices. More specifically, solvents as used herein is meant to include any water immiscible low molecular weight organic or silicone material added to the non-aqueous phase of an emulsion for the purpose of enhancing the formation of the emulsion, and is subsequently removed after the formation of the emulsion, such as evaporation during a drying or film formation step. Thus, the phrase "essentially free of solvent" is not meant to exclude the presence of solvent in minor quantities in process or emulsions of the present invention. For example, there may be instances where the components A) and B) may contain minor amounts of solvent as supplied commercially. Small amounts of solvent may also be present from residual cleaning operations in an industrial process. Preferably, the amount of solvent present should be less than 2% by weight of the mixture, and most preferably the amount of solvent should be less than 1% by weight of the dispersion.

The dispersion of step (I) may be prepared by combining components A) and B) and further mixing the components to form a emulsion. Mixing can be accomplished by any method known in the art to effect mixing of high viscosity materials. Mixing to form a homogeneous mixture is also referred to as homogenizing. The mixing may occur either as a batch, semi-continuous, or continuous process. Mixing may occur, for example using, batch mixing equipments with medium/low shear include change-can mixers, doubleplanetary mixers, conical-screw mixers, ribbon blenders, double-arm or sigma-blade mixers; batch equipments with high-shear and high-speed dispersers include those made by Charles Ross & Sons (NY), Hockmeyer Equipment Corp. (NJ); batch mixing equipment such as those sold under the tradename Speedmixer®; batch equipments with high shear actions include Banbury-type (CW Brabender Instruments Inc., NJ) and Henschel type (Henschel mixers America, TX). Illustrative examples of continuous mixers/compounders include extruders single-screw, twin-screw, and multi-screw extruders, co-rotating extruders, such as those manufactured by Krupp Werner & Pfleiderer Corp (Ramsey, N.J.), and Leistritz (NJ); twin-screw counter-rotating extruders, two-stage extruders, twin-rotor continuous mixers, dynamic or static mixers or combinations of these equipments.

The process of combining and mixing components A) and B) may occur in a single step or multiple step process. Thus, components A) and B) may be combined in total, and subsequently mixed via any of the techniques described above. Alternatively, a portion(s) of components A) and B) may first be combined, mixed, and followed by combining additional quantities of either or both components and further mixing. One skilled in the art would be able to select optimal portions of components A) and B) for combing and mixing, depending on the selection of the quantity used and the specific mixing techniques utilized to perform step I) to provide a dispersion of components A) and B).

Step II of the process involves forming an emulsion. Optionally, water can be added from 5 to 700 parts water to every 100 parts of the step I dispersion to dilute the emulsion. In one embodiment the emulsion formed is a water continuous emulsion. Typically, the water continuous emulsion has dispersed particles of the silicone gum from step I, and having an average particle size less than 150 µm.

The optional water added to the mixture from step I is at such a rate so as to form an emulsion of the dispersion of step I. While this amount of water can vary depending on the selection of the amount of silicone present and the specific ethylene oxide/propylene oxide content of component B), generally the amount of water is from 5 to 700 parts per 100 parts by weight of the step I dispersion, alternatively from 5 to 100 parts per 100 parts by weight of the step I dispersion, or alternatively from 5 to 70 parts per 100 parts by weight of the step I dispersion.

Alternatively, a portion or all the water used in step II) may be substituted with various hydrophilic solvents that are soluble with water such as low molecular weight alcohols, ethers, esters or glycols. Representative non-limiting examples include low molecular weight alcohols such as methanol, ethanol, propanol, isopropanol and the like; low molecular weight ethers such as di(propyleneglycol) mono methyl ether, di(ethyleneglycol) butyl ether, di(ethyleneglycol) methyl ether, di(propyleneglycol) butyl ether, di(propyleneglycol) methyl ether acetate, di(propyleneglycol) propyl ether, ethylene glycol phenyl ether, propylene glycol butyl ether, 1-methoxy-2-propanol, 1-methoxy-2-propyl acetate, propylene glycol propyl ether, 1-phenoxy-2-propanol, tri(propyleneglycol) methyl ether and tri(propyleneglycol) butyl ether, and other like glycols.

Mixing and homogenizing in step (II) can be accomplished by any method known in the art to affect mixing of high viscosity materials. The mixing may occur either as a batch, semi-continuous, or continuous process. Any of the mixing methods as described for step (I), may be used to affect mixing in step (II). Typically, the same equipment is used to effect mixing in steps I) and II).

Optionally, the water continuous emulsion formed in step (II) may be further sheared according to step (III) to reduce particle size and/or improve long term storage stability. The shearing may occur by any of the mixing techniques discussed above.

The emulsion products resulting from the present process may be an oil-in-water emulsion. The particle size may be determined by light scattering. Suitable light scattering techniques used to measure emulsion particle size are well known in the art. The particle size is obtained from a particle size distribution (PSD). The PSD can be determined on a volume, surface, length basis. The volume particle size is equal to the diameter of the sphere that has the same volume as a given particle. The term Dv represents the average volume particle size of the dispersed particles. Dv 50 is the particle size measured in volume corresponding to 50% of the cumulative particle population. In other words if Dv 50=10 µm, 50% of the particle have an average volume particle size below 10 µm and 50% of the particle have a volume average particle size above 10 µm. Dv 90 is the particle size measured in volume corresponding to 90% of the cumulative particle population.

The average volume particle size of the dispersed silicone particles in the oil-in-water emulsions is between 0.1 µm and 150 µm; or between 0.1 µm and 30 µm; or between 0.3 µm and 5.0 µm.

Silicone content of the present emulsion may vary from 0.5 weight percent to 95 weight percent, alternatively from 10 weight percent to 95 weight percent, or alternatively from 40 weight percent to 80 weight percent.

The water dilutable silicone emulsions of the present invention may contain other components on an optional basis insofar as the object of the present invention is not impaired. For example, inorganic fillers such as quartz, biocides when water is present, untreated and treated silicas, metal hydroxide micropowders such as aluminum hydroxide micropowder, calcium hydroxide micropowder, and magnesium hydroxide micropowder, bis amides such as those disclosed in U.S. Pat. No. 5,192,336, flake-form fillers such as mica, dimethylpolysiloxanes, epoxy-functional diorganopolysiloxanes, and amino-functional diorganopolysiloxanes, as well as pigments, corrosion inhibitors, and dyes can be added to the emulsions. Additional components that may also be included in the emulsions may be preservatives, freeze/thaw additives, and various thickeners.

In one embodiment, the present emulsions can comprise as an additive an acrylic emulsion or a polyurethane dispersion, for example, for making a coating composition. The coating compositions can comprise:
  i) 1 to 99 weight percent of an acrylic emulsion or a polyurethane dispersion;
     alternatively 10 to 99 weight percent of an acrylic emulsion or a polyurethane dispersion,
     alternatively 50 to 99 weight percent of an acrylic emulsion or a polyurethane dispersion, or
     alternatively 90 to 99 weight percent of an acrylic emulsion or a polyurethane dispersion,
  ii) 0.01 to 95 weight percent of a silicone emulsion as described above;
     alternatively 0.01 to 20 weight percent of the silicone emulsion,
     alternatively 1 to 15 weight percent of the silicone emulsion, or
     alternatively 1 to 10 weight percent of the silicone emulsion, and iii) 0 to 90 weight percent of an organic solvent;
   alternatively 1 to 90 weight percent of an organic solvent,
   alternatively 1 to 50 weight percent of an organic solvent, or
   alternatively 1 to 15 weight percent of an organic solvent.

As used herein "acrylic emulsion" refers to any water based emulsion of a polyacrylate, polymethacrylate, or other similar copolymers derived from acrylic or methacrylic acid. Many acrylic emulsions are available commercially for ready use in paints and coating formulations. These acrylic emulsions are often described as self-crosslinkable acrylic emulsions, which may be used in the present coating compositions. Representative self-crosslinkable acrylic emulsions include useful in the present compositions include; ALBERDINGK AC 2514, ALBERDINGK AC 25142, ALBERDINGK AC 2518, ALBERDINGK AC 2523, ALBERDINGK AC 2524, ALBERDINGK AC 2537, ALBERDINGK AC 25381, ALBERDINGK AC 2544, ALBERDINGK AC 2546, ALBERDINGK MAC 24, and ALBERDINGK MAC 34 polymer dispersions from Alberdingk Boley, Inc.; EPS 2538 and EPS 2725 acrylic emulsions from EPS Corp.; RHOPLEX™ 3131-LO, RHOPLEX E-693, RHOPLEX E- 940, RHOPLEX E-1011, RHOPLEX E-2780, RHOPLEX HG-95P, RHOPLEX HG-700, RHOPLEX HG-706, RHOPLEX PR-33, RHOPLEX TR-934HS, RHOPLEX TR-3349 and RHOPLEX™VSR-1050 acrylic emulsions from Rohm and Haas Co.; RHOSHIELD™ 636 and RHOSHIELD 3188 polymer dispersions from Rohm and Haas Co; JONCRYL® 8380, 8300, 8211, 1532, 1555, 2560, 1972, 1980, 1982, and 1984 acrylic emulsions from BASF Corp.; NEOCRYL™ A-1127, NEOCRYL A-6115, NEOCRYL XK-12, NEOCRYL XK-90, NEOCRYL XK-98 and NEOCRYL XK-220 acrylic latex polymers from DSM NeoResins, Inc., and mixtures thereof. In one embodiment, the acrylic emulsion is JONCRYL® 8383 acrylic emulsion from BASF Corp.

The polyurethane dispersion useful in the present invention can be an aqueous dispersion of a polyurethane resin prepared by dispersing polyurethane resin in water in the presence of a dispersant. The dispersant may include nonionic surfactants, anionic surfactants, cationic surfactants, amphoteric surfactants, and other emulsifying and dispersing agents useful for preparing aqueous dispersions. The dispersant may be used singly or in a combination of two or more kinds.

Examples of dispersant include, but is not limited to, nonionic, anionic, ionic, cationic, zwitterionic, or mixtures of nonionic with cationic, anionic or zwitterionic surfactants. In one embodiment, the dispersant may be a nonionic or an anionic surfactants. Examples of dispersants, include but is not limited to, polyoxyalkylene modified nonionic surfactants, polyhydric alcohol nonionic surfactants, esters and ethers of carboxylic acids containing hydrocarbon groups having 8 to 24 carbon atoms or salts thereof, for example, sodium lauryl ether acetate, and sodium (poly)oxyethylene lauryl ether acetate, sulfuric acid esters or ether of sulfuric acid esters containing hydrocarbon groups having 8 to 24 carbon atoms and salts thereof, for example, sodium lauryl sulfate, sodium (poly)oxyethylene lauryl sulfate, triethanolamine (poly)oxyethylene lauryl sulfate, and sodium (poly)oxyethylene coconut oil fatty acid monoethanol amide sulfate, salts of sulfonic acids containing hydrocarbon groups having 8 to 24 carbon atoms, for example, sodium dodecylbenzene sulfonate, salts of sulfosuccinic acids containing one or two hydrocarbon groups having 8 to 24 carbon atoms; phosphoric acid esters or ether of phosphoric acid esters containing hydrocarbon groups having 8 to 24 carbon atoms and salts thereof, for example, sodium lauryl phosphate, sodium (poly)oxyethylene lauryl ether phosphate, salts of fatty acids containing hydrocarbon groups having 8 to 24 carbon atoms, for example, sodium laurate, triethanolamine laurate, salts of acylated amino acids containing hydrocarbon groups having 8 to 24 carbon atoms, for example, sodium coconut oil fatty acid methyl taurin, sodium coconut oil fatty acid sarcosine, triethanolamine coconut oil fatty acid sarcosine, triethanolamine N-coconut oil fatty acid acyl-L-glutamate, sodium N-coconut oil fatty acid acyl-L-glutamate, and sodium lauroyl methyl-β-alanine, quaternary ammonium salt, for example, stearyltrimethylammonium chloride, behenyltrimethylammonium chloride, distearyldimethylammonium chloride, and lanolin fatty acid aminopropylethyldimethylammonium ethyl sulfate, amine salt, for example, lactic acid salt of diethylaminoethyl stearamide, dilaurylamine hydrochloride, and oleylamine lactate, betaine-type amphoteric surfactants, for example, coconut oil fatty acid amide propyl dimethylamino acetic acid betaine, lauryl dimethylamino acetic acid betaine, 2-alkyl-N-carboxymethyl-N-hydroxyethyl imidazolinium betaine, lauryl hydroxy sulfobetaine, and sodium lauroyl amidoethyl hydroxyethyl carboxymethyl betaine hydroxypropyl phosphate, amino acid-type amphoteric surfactants, for example, sodium β-lauryl aminopropionate, polyvinyl alcohol; starch and derivatives thereof; cellulose derivatives such as carboxymethyl cellulose, methyl cellulose, hydroxyethyl cellulose, carboxyl group-containing (co)polymers such as sodium polyacrylate; and emulsifying and dispersing agents having urethane groups or ester groups.

Additional examples of dispersants can be metal or ammonia salts of sulfonates, phosphates and carboxylates, alkali metal salts of fatty acids such as sodium stearate, sodium palmitate, potassium oleate, alkali metal salts of fatty acid sulfates such as sodium lauryl sulfate, the alkali metal salts of alkylbenzenesulfones and alkylnaphthalenesulfones such as sodium dodecylbenzenesulfonate, sodium alkylnaphthalene-sulfonate; alkali metal salts of dialkyl-sulfosuccinates; the alkali metal salts of sulfated alkylphenol ethoxylates such as sodium octylphenoxypolyethoxyethyl sulfate; alkali metal salts of polyethoxyalcohol sulfates, alkali metal salts of polyethoxyalkylphenol sulfates, sodium dodecyl benzene sulfonate, sodium dodecyl sulfonate, sodium dodecyl diphenyl oxide disulfonate, sodium n-decyl diphenyl oxide disulfonate, isopropylamine dodecylbenzenesulfonate, sodium hexyl diphenyl oxide disulfonate, and ethylene oxide adducts of phenols, such as nonyl phenol.

In general, dispersant is added in sufficient amount so as to render a dispersion having an average particle size wherein 50 and 1000 nm and a polydispersity of from 1.0 to 2.0. The content of the dispersant is based on the weight of the polyurethane resin, and is generally 0.01 to 20 weight percent, preferably 0.1 to 10 weight percent, and more preferably 1 to 5 weight percent.

The water dilutable silicone emulsions may contain co-solvents or diluents. The co-solvents can be selected from the group consisting of ethylene glycol, propylene glycol, polypropylene glycol, polyethylene glycol, copolymers of ethylene and propylene glycols, condensates of polypropylene glycol with polyols, condensates of polyethylene glycol with polyols, condensates of copolymers of ethylene and propylene glycols with polyols, alcohol alkoxylates, and alkylphenol alkoxylates. The co-solvent may be an organic solvent. The organic solvent may be selected from any organic solvents that are typically used to prepare coating compositions. The organic solvent may include a combination of two or more solvents. When used in the coating compositions, the organic solvent may be present in compositions up to a maximum of 90 weight percent of the composition.

In one embodiment, the organic solvent is a glycol solvent. The glycol solvent helps reduce viscosity and may aid wetting or film coalescence. Representative glycol solvents include ethylene glycol, ethylene glycol methyl ether, ethylene glycol ethyl ether, ethylene glycol monobutyl ether, ethylene glycol-2-ethylhexyl ether, propylene glycol, propylene glycol methyl ether, propylene glycol ethyl ether, propylene glycol monobutyl ether, propylene glycol-2-ethylhexyl ether, diethylene glycol, diethylene glycol methyl ether, diethylene glycol ethyl ether, diethylene glycol monobutyl ether, diethylene glycol-2-ethylhexyl ether, dipropylene glycol, dipropylene glycol methyl ether, dipiopylene glycol ethyl ether, dipiopylene glycol monobutyl ether, dipropylene glycol-2-ethylhexyl ether, and mixtures thereof hydrophilic glycol solvents (e.g., propylene glycol methyl ether or dipropylene glycol monomethyl ether) are preferred.

In one embodiment, the organic solvent is an alcohol. Representative alcohol solvents include both lower molecular weight alcohols; such as methanol, ethanol, propanol, and butanol; as well as branched hydrocarbyl based alcohols like Texanol® solvents; such as 2,2,4-Trimethyl-1,3-pentanediolmono(2-methylpropanoate). In a further embodiment, the organic solvent is a combination of a glycol and alcohol, as described above.

The co-solvent may be present in an amount from 0 to 20 weight percent, or 0 to 10 weight percent, or 1 to 10 weight percent, or 1 to 5 weight percent of the weight of the water dilutable silicone emulsion.

The water dilutable silicone emulsions may contain co-surfactants. Examples co-surfactants include, but are not limited to, non-ionic surfactants, amphoteric surfactants, condensates of ethylene oxide with long chain fatty alcohols or fatty acids such as a alcohol having 12 to 16 carbon atoms, condensates of ethylene oxide with an amine or an amide, condensation products of ethylene and propylene oxide, esters of glycerol, sucrose, sorbitol, fatty acid alkylol amides, sucrose esters, fluoro-surfactants, fatty amine oxides, polyoxyalkylene alkyl ethers such as polyethylene glycol long chain (12 to 14 carbon atoms) alkyl ether, polyoxyalkylene sorbitan ethers, polyoxyalkylene alkoxylate esters, polyoxyalkylene alkylphenol ethers, ethylene glycol propylene glycol copolymers and alkylpolysaccharides. Examples of alkylpolysaccharides are materials of structure $R^7$—O—$(R^8O)_u$—$(G)_v$, wherein $R^7$ represents a linear or branched alkyl group, a linear or branched alkenyl group or an alkylphenyl group, $R^8$ represent an alkylene group, G represents a reduced sugar, u denotes 0 or a positive integer and v represent a positive integer. U.S. Pat. No. 5,035,832 describe certain useful alkylpolysaccharides. Non-ionic surfactants additionally include polymeric surfactants such as polyvinyl alcohol (PVA) and polyvinylmethylether.

Representative examples of suitable commercially available non-ionic surfactants include polyoxyethylene fatty alcohols sold under the tradename BRIJ® by Croda. Some examples are BRIJ® L23, an ethoxylated alcohol known as polyoxyethylene (23) lauryl ether, and BRIJ® L4, another ethoxylated alcohol known as polyoxyethylene (4) lauryl ether. Some additional non-ionic surfactants include ethoxylated alcohols sold under the trademark Novel TDA® (Sasol North America, Houston, Tex.) and TERGITOL® (The Dow Chemical Company, Midland, Mich.). Some example are TERGITOL® TMN-6, an ethoxylated alcohol known as ethoxylated trimethylnonanol; and various of the ethoxylated alcohols, i.e., the 12-14 carbon atoms secondary alcohol ethoxylates, sold under the trademarks TERGITOL® 15-S-5, TERGITOL® 15-S-12, TERGITOL® 15-S-15, TERGITOL® 15-S-30, TERGITOL® 15-S-40, Novel TDA9®, Novel TDA40® and Novel TDA150®. Co-surfactants containing silicon atoms may also be used.

Examples of suitable amphoteric surfactants include imidazoline compounds, alkylaminoacid salts, and betaines. Specific examples include cocamidopropyl betaine, cocamidopropyl hydroxysulfate, cocobetaine, sodium cocoamidoacetate, cocodimethyl betaine, N-coco-3-aminobutyric acid and imidazolinium carboxyl compounds. Representative examples of suitable amphoteric surfactants include imidazoline compounds, alkylaminoacid salts, and betaines.

In one embodiment, the co-surfactant may be a poly(oxyethylene)-poly(oxypropylene)-poly(oxyethylene) tri-block copolymer. Poly(oxyethylene)-poly(oxypropylene)-poly(oxyethylene) tri-block copolymers are also commonly known as Poloxamers. They are nonionic triblock copolymers composed of a central hydrophobic chain of polyoxypropylene (poly(propylene oxide)) flanked by two hydrophilic chains of polyoxyethylene (poly(ethylene oxide)). Poly(oxyethylene)-poly(oxypropylene)-poly(oxyethylene) tri-block copolymers are commercially available from BASF (Florham Park, N.J.) and are sold under the tradename PLURONIC®. Representative, non-limiting examples suitable as component (B) include; PLURONIC® F127, PLURONIC® F98, PLURONIC® F88, PLURONIC® F87, PLURONIC® F77 and PLURONIC® F68, and PLURONIC® F-108.

In another embodiment, the co-surfactant is a tetrafunctional poly(oxyethylene)-poly(oxypropylene) block copolymer derived from the sequential addition of propylene oxide and ethylene oxide to ethylene diamine. These tetra-functional block copolymers are also commonly known as Poloxamines. Tetrafunctional poly(oxyethylene)-poly(oxypropylene) block copolymers are commercially available from BASF (Florham Park, N.J.) and are sold under the tradename TETRONIC®. Representative, non-limiting examples suitable as component (B) include; TETRONIC® 908, TETRONIC® 1107, TETRONIC® 1307, TETRONIC® 1508 and TETRONIC® 1504.

The co-surfactant may be present in an amount from 0 to 20 weight percent, or 0 to 10 weight percent, or 1 to 10 weight percent, or 1 to 5 weight percent of the weight of the water dilutable silicone emulsion.

The present silicone emulsions may be formulated into personal care products. The personal care compositions may be in the form of a cream, a gel, a powder, a paste, or a freely pourable liquid. Generally, such compositions can generally be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care products may be functional with respect to the portion of the body to which they are applied, cosmetic, therapeutic, or some combination thereof. Conventional examples of such products include, but are not limited to: antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

The compositions according to this invention can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the compositions according to the present invention may be used in a conventional manner for example for conditioning the skin. An effective amount of the composition for the purpose is applied to the skin. Such effective amounts generally range from about 1 mg/cm$^2$ to about 3 mg/cm$^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The water dilutable silicone emulsion of the present invention can be uses for coating composition to provide a continuous protective coating on a substrate by applying the composition to a surface of the substrate. Useful substrates include organic or inorganic components. Alternatively, substrates include at least one of household surfaces, leather, paper, wood, painted and unpainted surfaces, metal surfaces, plastics, fabric and in other applications where a protective coatings or architectural coatings is needed, and in paints.

In one embodiment, the present invention provides solid coatings prepared from the coating compositions of the present invention. In another embodiment, the present invention provides methods for preparing a solid coating comprising: i.) forming a film of the coating composition according to the present invention on a surface of a substrate; and ii.) removing water from the film to form the solid coating.

Having described the invention with reference to certain embodiments, other embodiments will become apparent to one skilled in the art from consideration of the specification. The invention is further defined by reference to the following examples describing the preparation of the emulsions and methods of the invention. It will be apparent to those skilled in the art that many modifications, both to materials and methods, may be practiced without departing from the scope of the invention.

The present invention is further illustrated by the following no limiting embodiments.

Embodiment 1. A silicone emulsion comprising:
A) 10 to 95 wt % of a silicone having a viscosity of at least 500,000 cP at 25° C.;
B) 0.1 to 30 wt % of a silicone polyether;
C) 0 to 90 wt % water;
D) 0 to 30 wt % of a co-surfactant; and
E) 0 to 30 wt % of a non-aqueous polar co-solvent,
wherein ratio of combined weight of D) and E) to B) is from 0 to 5.

Embodiment 2. A silicone emulsion comprising:
A) 10 to 95 wt % of a silicone having a viscosity of at least 500,000 cP at 25° C.;
B) 0.1 to 30 wt % of a silicone polyether obtainable by reacting
  i) SiH functional polyorganosiloxane,
  ii) monoalkenyl functional polyoxyalkylene,
  iii) optionally dialkenyl functional polyorganosiloxane,
wherein the molar ratio of SiH to alkenyl in (ii) is from 1:1 to 30:1 and the molar ratio of SiH to alkenyl in optional (iii) is from 1:0.01 to 1:1 with the proviso that the total alkenyl:SiH is from 1.5:1 to 1:1;
C) optionally sufficient amount of water to sum all ingredients of the emulsion to 100 weight percent.

Embodiment 3. The silicone emulsion according to Embodiment 2, further comprising D) a co-surfactant, where weight ratio of D) to B) is no greater than 5.

Embodiment 4. The silicone emulsion according to Embodiment 2, further comprising E) a non-aqueous polar co-solvent, where weight ratio of E) to B) is no greater than 5.

Embodiment 5. The silicone emulsion according to Embodiment 2, further comprising:
D) a co-surfactant,
E) a non-aqueous polar co-solvent,
wherein ratio of combined weight of D) and E) to B) is no greater than 5.

Embodiment 6. The silicone emulsion according to any one of Embodiments 2 and 3, wherein the SiH functional polyorganosiloxane has average formula

$$R_3SiO(RRSiO)_x(R^1RSiO)_ySiR_3 \quad (I)$$

wherein each R is independently an alkyl having 1 to 6 carbon atoms or an aryl having 6 to 10 carbon atoms, R$^1$ is hydrogen, x is 1 to 1000, and y is 1 to 100 and the dialkenyl functional polyorganosiloxane is a vinyl terminal polydimethylsiloxane.

Embodiment 7. The silicone emulsion according to Embodiment 5, wherein the monoalkenyl functional polyoxyalkylene is a monoalkenyl functional ethylene oxide/propylene oxide copolymer having an average formula

$$CH_2=CH^2(CH_2)_n—[(C_2H_4O)_c(C_3H_6O)_d]—OR^2 \quad (II)$$

wherein R$^2$ is hydrogen or an alkyl having 1 to 12 carbon atoms, and R$^3$ is hydrogen, acyl, or an alkyl having 1 to 12 carbon atoms; c is from 1 to 400, d is from 0 to 100, n is 0 to 10, wherein the ratio of c/(c+d) is from 0.5 to 1.

Embodiment 8. A silicone emulsion comprising:
A) 10 to 95 wt % of a silicone having a viscosity of at least 500,000 cP at 25° C.;
B) 0.1 to 30 wt % of a silicone polyether obtainable by reacting
  i) SiH functional polyorganosiloxane,
  ii) dialkenyl functional polyoxyalkylene,
wherein the molar ratio of SiH to alkenyl in (ii) is from 1:1 to 1:2.5;
C) optionally sufficient amount of water to sum all ingredients of the emulsion to 100 weight percent.

Embodiment 9. The silicone emulsion according to Embodiment 8 further comprising D) a co-surfactant.

Embodiment 10. The silicone emulsion according to Embodiment 8 further comprising E) a non-aqueous polar solvent.

Embodiment 11. The silicone emulsion according to Embodiment 8 further comprising D) a co-surfactant and E) a non-aqueous polar co-solvent, where ratio of combined weight of D) and E) to B) is no greater than 5.

Embodiment 12. The silicone emulsion according to Embodiments 8-11, wherein the SiH functional polyorganosiloxane has average formula

$$RRR^1SiO(RRSiO)_xSiRRR^1 \quad (III)$$

wherein each R is independently an alkyl having 1 to 6 carbon atoms or an aryl having 6 to 10 carbon atoms, $R^1$ is hydrogen, x is 1 to 1000.

Embodiment 13. The silicone emulsion according to Embodiments 8-11, wherein the dialkenyl functional polyoxyalkylene is a dialkenyl functional ethylene oxide/propylene oxide copolymer having the average formula

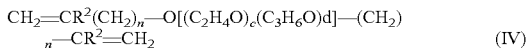

$$CH_2=CR^2(CH_2)_n-O[(C_2H_4O)_c(C_3H_6O)_d]-(CH_2)_n-CR^2=CH_2 \quad (IV)$$

wherein $R^2$ is hydrogen or an alkyl having 1 to 12 carbon atoms, c is from 1 to 400, d is from 0 to 100, n is 0 to 10, wherein the ratio of c/(c+d) is from 0.5 to 1.

Embodiment 14. The silicone emulsion according to any one of the preceding Embodiments, wherein the silicone is a hydroxy terminated polydimethylsiloxane having a viscosity of at least 1,000,000 cP at 25° C.

Embodiment 15. The silicone emulsion according to any one of the preceding Embodiments, wherein the silicone is a vinyl terminated polydimethylsiloxane having a viscosity of at least 1,000,000 cP at 25° C.

Embodiment 16. The silicone emulsion according to any one of the preceding Embodiments, wherein the silicone polyether has a weight average molecular weight greater than 10,000 g/mol.

Embodiment 17. The silicone emulsion according to any one of the preceding Embodiments, wherein the emulsion comprises water and is an aqueous continuous emulsion.

Embodiment 18. The silicone emulsion according to any one of the preceding Embodiments, wherein the silicone polyether is water soluble or water dispersable.

Embodiment 19. A coating composition comprising:
A) 10-95% of the silicone emulsion of any one of claims 1 to 18;
B) 1 to 99 weight percent of an acrylic emulsion or a polyurethane dispersion;
C) 0 to 90 weight percent of a polar organic solvent.

Embodiment 20. A process for making a silicone emulsion comprising:
I) forming a dispersion by combining:
  A) 10 to 95 wt % of a silicone having a viscosity of at least 500,000 cP at 25° C.;
  B) 0.1 to 30 wt % of a silicone polyether obtainable by reacting
    i) SiH functional polyorganosiloxane,
    ii) monoalkenyl functional polyoxyalkylene,
    iii) optionally a dialkenyl functional polyorganosiloxane,
  wherein the molar ratio of SiH to alkenyl (ii) is from 1:1 to 30:1 and the molar ratio of SiH to alkenyl in (iii) is from 1:0.01 to 1:1 with the proviso that the total alkenyl:SiH is from 1.5:1 to 1:1; and
  C) optionally a co-surfactant or co-solvent;
II) mixing and homogenizing A), B) and optionally C) from step I) to form a silicone emulsion; and
III) optionally, adding water or other polar additives to the silicone emulsion.

Embodiment 21. The process according to Embodiment 20, further comprising in step II) adding 5 to 700 parts water for every 100 parts of the step I) dispersion and mixing and homogenizing A), B), optionally C) and the water to form the silicone emulsion.

Embodiment 22. The process according to any one of Embodiments 20 to 21, wherein the silicone is a silicone gum that is a hydroxy terminated polydimethylsiloxane having a viscosity of at least 500 thousand cP at 25° C.

Embodiment 23. The process according to any one of Embodiments 20 to 22, wherein the SiH functional polyorganosiloxane has average formula

$$R_3SiO(RRSiO)_x(R^1RSiO)_ySiR_3 \quad (I)$$

wherein each R is independently an alkyl having 1 to 6 carbon atoms or an aryl having 6 to 10 carbon atoms, $R^1$ is hydrogen, x is 1 to 1000, and y is 1 to 100.

Embodiment 24. The process according to any one of Embodiments 20 to 23, wherein the monoalkenyl functional polyoxyalkylene is a monoalkenyl functional ethylene oxide/propylene oxide copolymer.

Embodiment 25. The process according to any one of Embodiment 22 to 24, wherein the monoalkenyl functional ethylene oxide/propylene oxide copolymer has average formula

$$CH_2=CH^2(CH_2)_n-[(C_2H_4O)_c(C_3H_6O)_d]-OR^2 \quad (II)$$

wherein $R^2$ is hydrogen or an alkyl having 1 to 12 carbon atoms, and $R^3$ is hydrogen, acyl or an alkyl having 1 to 12 carbon atoms; c is from 1 to 400, d is from 0 to 100, n is 0 to 10, wherein the ratio of c/(c+d) is from 0.5 to 1.

Embodiment 26. The process according to any one of Embodiment 20 to 25, wherein the dialkenyl functional polyorganosiloxane is a vinyl terminal polydimethylsiloxane.

Embodiment 27. The process according to Embodiment 20, wherein the co-surfactant is present and ratio of co-surfactant to B) is no greater than 5.

Embodiment 28. The process according to Embodiment 20, wherein the co-solvent is present and a non-aqueous polar co-solvent and ratio of co-solvent to B) is no greater than 5.

Embodiment 29. The process according to Embodiment 20, wherein the co-surfactant and co-solvent are present, wherein the co-solvent is a non-aqueous polar co-solvent and wherein ratio of combined weight of co-surfactant and co-solvent to B) is no greater than 5.

Embodiment 30. A process for making a silicone emulsion comprising:
I) forming a dispersion by combining:
  A) 10 to 95 wt % of a silicone having a viscosity of at least 500,000 cP at 25° C.;
  B) 0.1 to 30 wt % of a silicone polyether obtainable by reacting
    i) terminal di-SiH functional polyorganosiloxane,
    ii) dialkenyl functional polyoxyalkylene,
  wherein the molar ratio of SiH to alkenyl in (ii) is from 1:1 to 1:2.5;
  C) optionally a co-surfactant or co-solvent;
II) mixing and homogenizing A), B) and optionally C) from step I) to form a silicone emulsion; and
III) optionally, adding water or other polar additives to the silicone emulsion.

Embodiment 31. The process according to Embodiment 30, wherein the co-surfactant is present.

Embodiment 32. The process according to Embodiment 30, wherein the co-solvent is present and is a non-aqueous polar solvent.

Embodiment 33. The process according to Embodiment 30, wherein the co-surfactant and co-solvent are present, wherein the co-solvent is a non-aqueous polar co-solvent and wherein ratio of combined weight of co-surfactant and co-solvent to B is no greater than 5.

Embodiment 34. Use of a silicone emulsion according to any one of Embodiments 1 to 19 for applying to a surface of a substrate to form a coating of the silicone emulsion on the surface.

Embodiment 35. Use of a silicone emulsion according to any one of Embodiments 1 to 19 in a skin care product, hair care product, personal care product, household care product or automobile care product.

Embodiment 36. Use of a silicone emulsion according to any one of Embodiments 1 to 19 in coating applications having from 0.5 to 5% by weight of a coalescing agent.

EXAMPLES

The following examples are included to demonstrate certain embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain the same or similar result without departing from the spirit and scope of the invention. All percentages are in weight percent. All measurements were conducted at 23° C. unless indicated otherwise.

Example 1

Silicone Emulsion Using a Silicone Polyether (SPE)

In a 150 mL polypropylene cup were added 50 grams of a silicone gum of a viscosity of 20 million cP and 10 grams of a water soluble branched silicone polyether having a nominal formula weight of 28,000 g/mol. The content was mixed in the Speed Mixer™ DAC 150FV for 60 seconds at 2500 rpm. The process was repeated two more times at 3000 rpm. To the content was added a total of 40 grams of water in three increments, each addition followed by mixing for 60 seconds at 3000 rpm in the same mixer. This arrived at a homogeneous white emulsion.

Example 2

Coating Formulation

To 50 grams of a polyurethane dispersion (PUD) was added 5 grams of the silicone emulsion of Example 1 to arrive at a silicone active content of 2.5%. The content was mixed using an Ika mixer equipped with a propeller blade at 1000 rpm for 10 minutes. The mixture was let rest for 10 minutes to defoam.

Coating test was performed as follows. 5 ml of the above formulation was coated onto a varnished cardboard (Form 2A opacity chart from Lenetta®) using a 30 micron cylindrical applicator (from Elcometer®: Baker applicator 3520). After the application, the coated cardboard was dried in a conventional oven set at a temperature of 80° C. for 2 minutes. The coated cardboard was then visually inspected to detect defects such as craters and pinholes on the surface of the coating. Assessment was recorded by counting the number of defects per 140 mm by 250 mm area. The same assessment was done using a glass panel (15 cm by 20 cm) coated with the sample having the polyurethane dispersion and the silicone emulsion and cured under the same conditions as for the coated cardboard. The assessment on the coated glass panel was conducted visually and the same performance criteria were applied as done for the coated cardboard.

Comparative Example 1

Silicone Emulsion Using a Conventional Surfactant

In a 150 mL polypropylene cup were added 50 grams of silicone gum of viscosity of 20 million cP and 10 grams of Tergitol® 15-S-9. The content was mixed in the Speed Mixer™ DAC 150FV for 60 seconds at 2500 rpm. The mixing was repeated two more times at 3000 rpm. This resulted in an inhomogeneous mixture presented as globs of silicone gum co-existing with Tergitol 15-S-9 liquid. To the content was added 10 grams of water followed by mixing for 60 seconds at 3000 rpm in the same mixer. No emulsion was formed.

Comparative Example 2

Silicone Emulsion Using Pluronic® F-127

The procedure described above for Example 1 was followed except that Pluronic® F-127 was used in place of the branched silicone polyether.

Comparative Example 3

Emulsion Polymerized Silicone Emulsion Using Conventional Surfactant

An emulsion of a crosslinked polydimethylsiloxane having a dynamic viscosity of 100 million cP at 0.01 Hz obtained by emulsion polymerization and stabilized by a pair of surfactants laureth-4 and laureth-23 was used for comparative purpose.

Comparative Example 4

Comparative Coating Test

The table below provides observations about comparative coating test incorporating the various silicone emulsions prepared as described above.

| | Silicone additive | Coating Test | |
| --- | --- | --- | --- |
| Base binder | 2.5% active addition | On Leneta ® opacity chart | On glass panel |
| PUD | No silicone emulsion | No defect-transparent and glossy coating | No defect-transparent coating |
| PUD | Emulsion polymerized silicone emulsion using conventional surfactant (Comp. Ex. 3) | Transparent coating uniformly covered with >50 pin holes | Transparent coating uniformly covered with >50 pin holes and some bigger craters spread randomly on the surface |

-continued

| Base binder | Silicone additive 2.5% active addition | Coating Test On Leneta ® opacity chart | On glass panel |
|---|---|---|---|
| PUD | Silicone emulsion using SPE (Ex. 1) | Transparent coating with a few pin holes dispersed randomly on the surface | Transparent coating with a few pin holes dispersed randomly on the surface |
| PUD | Silicone emulsion using Pluronic ® F-127 (Comp. Ex. 2) | Opaque coating and orange peel effect | Opaque coating and orange peel effect |

Example 3

Following the procedure of Example 1, the following emulsions were made using the same silicone gum and the same branched silicone polyether (SPE).

|  | Wt % |  | Wt % |
|---|---|---|---|
| Silicone gum | 50 | Silicone gum | 50 |
| SPE | 4 | SPE | 4 |
| UCON 75 H 90000 | 4 | UCON 75 H 90000 | 4 |
| Tergitol 15-S-9 | 10 | Tergitol 15-S-40 | 10 |
| Water | 32 | Water | 32 |

Example 4

To a 250 mL three-necked round-bottom flask fitted with a nitrogen inlet, mechanical stirrer with Teflon paddle, and thermocouple, was added 24.98 g of a dimethylhydrogen-terminated polydimethylsiloxane of 20.5 degrees of polymerization, 62.50 g of poly((ethylene oxide)$_{50}$(propylene oxide)$_{17}$) dimethallyl ether, and 37.54 g isopropyl alcohol. The mixture was stirred at 200 rpm and heated to 75° C. under a nitrogen blanket. To the mixture was added 0.33 g of a solution of 1,3-divinyl-1,1,3,3-tetramethyldisiloxane platinum complex in isopropanol, containing 0.2% of elemental platinum. The mixture was stirred at 320 rpm at 75° C. for 4 hours. 38.71 g of Tergitol® 15-S-9 was added and the mixture was heated to 80° C. Vacuum was applied to strip off isopropyl alcohol from the mixture. The final product contains 69 wt% polydimethylsiloxane-poly(alkylene oxide) copolymer with a molecular weight of 31600, and 31 wt % Tergitol® 15-S-9.

Example 5

Step 1. In a Max-40 cup of the Speed Mixer™ DAC 150FVZ was added 16.8 grams of the silicone polyether from Example 4, 3.9 grams UCON™ 75H90000 and 9.3 grams Tergitol™ 15S9. The content was mixed at 3500 RPM for 30 seconds.

Step 2. In a Max-100 cup of the Speed Mixer™ DAC 150FVZ was added 35 grams of a silicone gum of viscosity 20 million cP, 16 grams of glass beads of 3 mm diameter and 10 grams of the mixture from step 1. The content was mixed at 3500 RPM for 2 minutes. The content was let cool to room temperature and mixing was repeated at 3500 RPM for another 2 minute. To the content was then added 2.5 grams water followed by mixing at 3500 RPM for 1 minute. An additional 22.5 grams of water was added in three increments, each followed by mixing at the same speed for 30 seconds. This arrived at a homogeneous white emulsion having a monomodal particle size distribution centered at 2.5 microns.

What is claimed is:

1. A silicone emulsion comprising:
   A) 10 to 95 wt % of a silicone having a viscosity of at least 500,000 cP at 25° C.;
   B) 0.1 to 30 wt % of a silicone polyether;
   C) 0 to 90 wt % of water;
   D) 0 to 30 wt % of a co-surfactant; and
   E) 0 to 30 wt % of a non-aqueous polar co-solvent;
   wherein the silicone polyether B) comprises a cross-linked reaction product comprising a polydiorganosiloxane-polyoxyalkylene copolymer in a block arrangement of segments comprising at least one of: (AB)p, A(BA)p and B(AB)p, wherein A denotes a polyoxyalkylene segment, B denotes a polydiorganosiloxane segment, and p is an integer greater than zero; and
   wherein the combined weight ratio of D) and E) to B) is from 0 to 5.

2. The silicone emulsion according to claim 1, wherein the silicone polyether B) is formed by reacting:
   i) a terminal di-SiH functional polyorganosiloxane; and
   ii) a dialkenyl functional polyoxyalkylene;
   wherein the molar ratio of SiH to alkenyl in ii) is from 1:1 to 1:2.5; and optionally, wherein a sufficient amount of water C) to sum all ingredients of the emulsion to 100weight percent is present.

3. The silicone emulsion according to claim 2, wherein:
   the co-surfactant D) is present; and/or
   the non-aqueous polar solvent E) is present;
   with the proviso that if both D) and E) are present, the combined weight ratio of D) and E) to B) is no greater than 5.

4. The silicone emulsion according to claim 2, wherein the SiH functional polyorganosiloxane i) has the average formula

$$RRR^1SiO(RRSiO)_xSiRRR^1 \qquad (III)$$

wherein each R is independently an alkyl having 1 to 6 carbon atoms or an aryl having 6 to 10 carbon atoms, $R^1$ is hydrogen, and x is 1 to 1,000.

5. The silicone emulsion according to claim 2, wherein the dialkenyl functional polyoxyalkylene ii) is a dialkenyl functional ethylene oxide/propylene oxide copolymer having the average formula

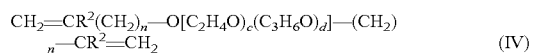
$$CH_2{=}CR^2(CH_2)_n{-}O[C_2H_4O)_c(C_3H_6O)_d]{-}(CH_2)_n{-}CR^2{=}CH_2 \qquad (IV)$$

wherein $R^2$ is hydrogen or an alkyl having 1 to 12 carbon atoms, c is from 1 to 400, d is from 0 to 100, n is 0 to 10, and the ratio of c/(c+d) is from 0.5 to 1.

6. The silicone emulsion according to claim 1, wherein the silicone A) is a polydimethylsiloxane having a viscosity of at least 1,000,000 cP at 25° C. and is hydroxy terminated or vinyl terminated.

7. The silicone emulsion according to claim 1, wherein the silicone polyether B) has a weight average molecular weight greater than 10,000 g/mol.

8. The silicone emulsion according to claim 1, wherein:
   the emulsion comprises water C) and is an aqueous continuous emulsion; and/or
   the silicone polyether B) is water soluble or water dispersible.

9. A silicone emulsion comprising:
A) 10 to 95 wt % of a silicone having a viscosity of at least 500,000 cP at 25° C.;
B) 0.1 to 30 wt % of a silicone polyether;
C) 0 to 90 wt % of water;
D) 0 to 30 wt % of a co-surfactant; and
E) 0 to 30 wt % of a non-aqueous polar co-solvent;
wherein the combined weight ratio of D) and E) to B) is from 0 to 5;
wherein the silicone polyether B) comprises a cross-linked reaction product formed by reacting:
i) a SiH functional polyorganosiloxane;
ii) a monoalkenyl functional polyoxyalkylene; and
iii) a dialkenyl functional polyorganosiloxane;
wherein the molar ratio of SiH to alkenyl in ii) is from 1:0.5 to 1:1.5 and the molar ratio of SiH to alkenyl in iii) is from 1:0.01 to 1:0.5, with the proviso that the total alkenyl:SiH is from 1.5:1 to 1:1; and
optionally, wherein a sufficient amount of water C) to sum all ingredients of the emulsion to 100 weight percent is present.

10. The silicone emulsion according to claim 9, wherein:
the co-surfactant D) is present, where the weight ratio of D) to B) is no greater than 5; and/or
the non-aqueous polar co-solvent E) is present, where the weight ratio of E) to B) is no greater than 5;
with the proviso that if both D) and E) are present, the combined weight ratio of D) and E) to B) is no greater than 5.

11. The silicone emulsion according to claim 9, wherein the SiH functional polyorganosiloxane i) has the average formula

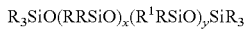

$$R_3SiO(RRSiO)_x(R^1RSiO)_ySiR_3 \quad (I)$$

wherein each R is independently an alkyl having 1 to 6 carbon atoms or an aryl having 6 to 10 carbon atoms, $R^1$ is hydrogen, x is 1 to 1,000, and y is greater than 1 to 100; and
wherein the dialkenyl functional polyorganosiloxane iii) is a vinyl terminal polydimethylsiloxane.

12. The silicone emulsion according to claim 9, wherein the monoalkenyl functional polyoxyalkylene ii) is a monoalkenyl functional ethylene oxide/propylene oxide copolymer having the average formula $$CH_2=CR^2(CH_2)_n-[(C_2H_4O)_c(C_3H_6O)_d]-OR^3 \quad (II)$$

wherein $R^2$ is hydrogen or an alkyl having 1 to 12 carbon atoms, $R^3$ is hydrogen, acyl, or an alkyl having 1 to 12 carbon atoms, c is from 1 to 400, d is from 0 to 100, n is 0 to 10, and the ratio of c/(c+d) is from 0.5 to 1.

13. A coating composition comprising:
a) the silicone emulsion according to claim 9;
b) an acrylic emulsion or a polyurethane dispersion; and
c) optionally, a polar organic solvent.

14. A process for making a silicone emulsion comprising:
I) forming a dispersion by combining:
A) 10 to 95 wt % of a silicone having a viscosity of at least 500,000 cP at 25° C.;
B) 0.1 to 30 wt % of a silicone polyether comprising a cross-linked reaction product formed by reacting:
i) a SiH functional polyorganosiloxane,
ii) a monoalkenyl functional polyoxyalkylene, and
iii) a dialkenyl functional polyorganosiloxane,
wherein the molar ratio of SiH to alkenyl ii) is from 1:0.5 to 1:1.5 and the molar ratio of SiH to alkenyl in iii) is from 1:0.01 to 1:0.5, with the proviso that the total alkenyl:SiH is from 1.5:1 to 1:1; and
C) optionally, a co-surfactant and/or co-solvent;
II) mixing and homogenizing A), B), and optionally C) from step I) to form the silicone emulsion; and
III) optionally, adding water and/or other polar additives to the silicone emulsion.

15. The process according to claim 14, further comprising in step II) adding 5 to 700 parts water for every 100 parts of the step I) dispersion and mixing and homogenizing A), B), optionally C) and the water to form the silicone emulsion.

16. The process according to claim 14, wherein:
the silicone A) is a silicone gum that is a hydroxy terminated polydimethylsiloxane;
the SiH functional polyorganosiloxane i) has the average formula

$$R_3SiO(RRSiO)_x(R^1RSiO)_ySiR_3 \quad (I)$$

wherein each R is independently an alkyl having 1 to 6 carbon atoms or an aryl having 6 to 10 carbon atoms, $R^1$ is hydrogen, x is 1 to 1,000, and y is greater than 1 to 100;
the monoalkenyl functional polyoxyalkylene ii) is a monoalkenyl functional ethylene oxide/propylene oxide copolymer; and
the dialkenyl functional polyorganosiloxane iii) is a vinyl terminal polydimethylsiloxane.

17. The process according to claim 16, wherein the monoalkenyl functional ethylene oxide/propylene oxide copolymer ii) has the average formula

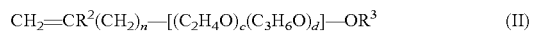

$$CH_2=CR^2(CH_2)_n-[(C_2H_4O)_c(C_3H_6O)_d]-OR^3 \quad (II)$$

wherein $R^2$ is hydrogen or an alkyl having 1 to 12 carbon atoms, $R^3$ is hydrogen, acyl, or an alkyl having 1 to 12 carbon atoms, c is from 1 to 400, d is from 0 to 100, n is 0 to 10, and the ratio of c/(c+d) is from 0.5 to 1.

18. The process according to claim 14, wherein:
the co-surfactant C1) is present, where the weight ratio of C1) to B) is no greater than 5; and/or
the co-solvent C2) is present and is a non-aqueous polar co-solvent, where the weight ratio of C2) to B) is no greater than 5;
with the proviso that if both C1) and C2) are present, the combined weight ratio of C1) and C2) to B) is no greater than 5.

19. A process for making a mechanical silicone emulsion comprising:
I) forming a dispersion by combining:
A) 10 to 95 wt % of a silicone having a viscosity of at least 500,000 cP at 25° C.; and
B) 0.1 to 30 wt % of a silicone polyether comprising a cross-linked reaction product formed by reacting
i) a terminal di-SiH functional polyorganosiloxane, and
ii) a dialkenyl functional polyoxyalkylene,
wherein the molar ratio of SiH to alkenyl in ii)is from 1:1 to 1:2.5; and
II) mixing and homogenizing A) and B) from step I) to form a silicone emulsion.

20. The process according to claim 19, wherein the step I) further comprises combining:
a co-surfactant C1); and/or
a co-solvent C2).

21. The process according to claim 19, further comprising adding water and/or other polar additives to the silicone emulsion.

22. The process according to claim 19, wherein the silicone polyether B) comprises a polydiorganosiloxane-polyoxyalkylene copolymer in a block arrangement of segments comprising at least one of: (AB)p, A(BA)p, and B(AB)p wherein A denotes a polyoxyalkylene segment, B denotes a polydiorganosiloxane segment, and p is an integer greater than zero.

* * * * *

UNITED STATES PATENT AND TRADEMARK OFFICE
CERTIFICATE OF CORRECTION

PATENT NO. : 10,385,212 B2  
APPLICATION NO. : 15/327274  
DATED : August 20, 2019  
INVENTOR(S) : Robert D. Kennedy et al.

Page 1 of 1

It is certified that error appears in the above-identified patent and that said Letters Patent is hereby corrected as shown below:

In the Claims

Column 30, Claim 5, Lines 51-52:
"$CH_2=CR^2(CH_2)_n-O[C_2H_4O)_c(C_3H_6O)_d]-(CH_2)_n-CR^2=CH_2$ (IV)"
Should read:
-- $CH_2=CR^2(CH_2)_n-O[(C_2H_4O)_c(C_3H_6O)_d]-(CH_2)_n-CR^2=CH_2$ (IV) --

Signed and Sealed this  
Tenth Day of December, 2019

Andrei Iancu  
*Director of the United States Patent and Trademark Office*